(12) United States Patent
Harris et al.

(10) Patent No.: US 7,745,431 B2
(45) Date of Patent: *Jun. 29, 2010

(54) PHARMACEUTICAL COMPOSITION OF 1-(3,4-DIMETHOXYPHENYL)-4-METHYL-5-ETHYL-7-METHOXY-8-HYDROXY-5H-2,3-BENZODIAZEPINE AND USES THEREOF

(75) Inventors: Herbert W. Harris, Merion, PA (US); Robert F. Kucharik, Glenmoore, PA (US); Steven M. Leventer, Langhorne, PA (US)

(73) Assignee: Vela Acquisition Corporation, Iselin, NJ (US)

( * ) Notice: Subject to any disclaimer, the term of this patent is extended or adjusted under 35 U.S.C. 154(b) by 757 days.

This patent is subject to a terminal disclaimer.

(21) Appl. No.: 10/728,261

(22) Filed: Dec. 3, 2003

(65) Prior Publication Data

US 2004/0157833 A1 Aug. 12, 2004

Related U.S. Application Data

(60) Provisional application No. 60/430,771, filed on Dec. 3, 2002.

(51) Int. Cl.
*A61K 31/55* (2006.01)
*A01N 43/62* (2006.01)
*C07D 243/14* (2006.01)

(52) U.S. Cl. ...................... 514/221; 540/569
(58) Field of Classification Search .............. 540/569; 424/244; 514/221
See application file for complete search history.

(56) References Cited

U.S. PATENT DOCUMENTS

| | | | |
|---|---|---|---|
| 3,736,315 A | 5/1973 | Kórósi et al. ............... 540/567 |
| 4,025,528 A | 5/1977 | Maeda et al. |
| RE30,014 E | 5/1979 | Korosi et al. |
| 4,322,346 A | 3/1982 | Kórósi et al. ............... 540/567 |
| 4,423,044 A | 12/1983 | Kórósi et al. ............... 514/221 |
| 4,614,740 A | 9/1986 | Láng et al. ................. 514/221 |
| 4,835,152 A | 5/1989 | Kórósi et al. ............... 514/220 |
| 4,840,948 A | 6/1989 | Láng et al. ................. 514/221 |
| 5,204,343 A | 4/1993 | Andrási et al. ............. 514/221 |
| 5,288,863 A | 2/1994 | Somogyi et al. ............ 540/567 |
| 5,457,118 A | 10/1995 | Dickinson et al. |
| 5,459,137 A | 10/1995 | Andrási et al. ............. 514/220 |
| 5,519,019 A | 5/1996 | Andrási et al. ............. 514/220 |
| 5,521,174 A | 5/1996 | Andrási et al. ............. 514/220 |
| 5,639,751 A | 6/1997 | Andrási et al. ............. 514/220 |
| 5,891,871 A | 4/1999 | Xia et al. ................... 514/219 |
| 6,075,018 A | 6/2000 | Vágó et al. ................. 514/221 |
| 6,080,736 A | 6/2000 | Landry ...................... 514/221 |
| 6,291,530 B1 | 9/2001 | Greenspan et al. |
| 6,638,928 B1 * | 10/2003 | Harris et al. ................ 514/221 |
| 6,649,607 B2 | 11/2003 | Leventer et al. ............ 514/221 |
| 6,683,072 B1 | 1/2004 | Kucharik et al. |
| 6,864,251 B2 * | 3/2005 | Kucharik et al. ........... 514/221 |
| 7,022,700 B2 | 4/2006 | Harris et al. ................ 514/221 |
| 7,078,398 B2 | 7/2006 | Leventer et al. ............ 514/221 |
| 2004/0138209 A1 | 7/2004 | Kucharik et al. |
| 2004/0138210 A1 | 7/2004 | Harris et al. |
| 2004/0152695 A1 | 8/2004 | Harris et al. ................ 514/221 |
| 2004/0157833 A1 | 8/2004 | Harris et al. |
| 2004/0162284 A1 | 8/2004 | Harris et al. |
| 2004/0224943 A1 | 11/2004 | Leventer et al. |
| 2004/0229866 A1 | 11/2004 | Harris et al. |
| 2004/0229867 A1 | 11/2004 | Kucharik ................... 514/221 |
| 2004/0254173 A1 | 12/2004 | Leventer et al. |
| 2005/0075329 A1 | 4/2005 | Leventer et al. |
| 2005/0288277 A1 | 12/2005 | Kucharik et al. |
| 2006/0166976 A1 | 7/2006 | Leventer et al. ............ 514/221 |
| 2007/0021412 A1 | 1/2007 | Kucharik et al. ........... 514/221 |
| 2007/0032479 A1 | 2/2007 | Leventer et al. |

FOREIGN PATENT DOCUMENTS

| | | |
|---|---|---|
| EP | 492 485 | 7/1992 |
| HU | 178516 | 3/1983 |
| HU | 178519 | 3/1983 |
| WO | 92/11262 | 7/1992 |
| WO | 00/24400 | 5/2000 |
| WO | 02/094189 | 11/2002 |
| WO | WO 02/088096 | 11/2002 |

OTHER PUBLICATIONS

Vermylen et al. "Thromboxane Synthase Inhibitors and Receptor Antagonists" 1992, Cardiovascular Drugs and Therapy, vol. 6, pp. 29-33.*
Gomtsyan et al. "Nonnucleoside inhibitos of adenosine kinase", 2004, Current Pharmaceutical Design, vol. 10, pp. 1093-1103.*
Riccioni et al. "Brief Review: Advances in Therapy with Antileukotriene Drugs", 2004, Annals of Clinicla and Laboratory Science, vol. 34, No. 4, pp. 379-387.*
Terasaka, T. "Non-nucloeside adenosine deaminase inhibitors: 2000-2004", Expert Opinion of Therapeutic Patents, Jul. 2005, vol. 15, No. 7, pp. 817-828.*
F. Gatta et al., "Derivatives of 2,3-Benzodiazepine(*)", Il Farmaco—Ed. Sc.—vol. 40—fasc. 12, pp. 942-955.
R. Sladká et al., "A Placebo-controlled Clinical Trial with Tofizopam * in the Treatment of Anxiety Neurosis" Divisions of Psychiatry, District Institutes of National Heatlth, Prague, 2 and 4; Psychiatric Department and Psychiatric Research Unity, Medical Scholl of Charles University, Prague, Czechoslovakia, pp. 176-180.
Edit J. Horváth et al., "Anxiolytic 2,3-benzodiazepines, their Specific Binding to the Basal Ganglia", Progress in Neurobiology vol. 60 (2000), pp. 309-342.

(Continued)

*Primary Examiner*—Sreeni Padmanabhan
*Assistant Examiner*—Kendra D Carter
(74) *Attorney, Agent, or Firm*—Drinker Biddle & Reath LLP

(57) ABSTRACT

Pharmaceutical compositions comprising 1-(3,4-dimethoxyphenyl)-4-methyl-5-ethyl-7-methoxy-8-hydroxy-5H-2,3-benzodiazepine; or a pharmaceutically acceptable salt thereof. The compositions are used for treating, preventing or delaying the onset of disorders mediated by $LTB_4$, $TXA_2$ or adenosine.

16 Claims, No Drawings

OTHER PUBLICATIONS

E. Tomori et al., "Investigation of the Metabolites of Tofizopam in Man and Animals by Gas-Liquid Chromatography-Mass Spectrometry", Journal of Chromatography, 241 (1982), pp. 89-99.

Eva Tomori et al., "Investigation of Metabolites of Tofizopam in Man and Animals", Polish Journal of Parmacology and Pharmacy, 1984, 36, pp. 423-430., PL ISSN 0301-0214.

Sharon Pellow et al., "The Effects of Tofisopam, a 3,4-Benzodiazepine, in Animal Models of Anxiety, Sedation, and Convulsions", Drug Development Research 7, pp. 61-73 (1986).

A. Bond et al., "A Comparison of the Psychotropic Profiles of Tofisopam and Diazepam", Fur J Clin Pharmacol (1982) 22, pp. 137-142.

J. Kanto et al., "Tofizopam: A Benzodiazepine Derivative Without Sedative Effect", International Journal of Clinical Pharmacology, Therapy and Toxicology, vol. 20 No. 7—1982, pp. 309-312.

T. Mennini et al., "Brain Levels of Tofizopam in the Rat and Relationship with Benzodiazepine Receptors", Naunyn-Schmiedeberg's Arch Pharmacol (1982) 321, pp. 112-115.

K. Maier et al., "The Effect of Tofisopam on Psychic Performance in Persons with More than Average Anxiety: A Controlled Experimental Trial", Current Therapeutic Research, vol. 35, No. 4, Apr. 1984, pp. 541-548.

Chihiro Ito, Behavioral Pharmacological Study of the Structure-Activity Relationship of Benzodiazepine Derivatives—with Particular Reference to the Activity of 2,3-Benzodiazepine-, (1981) 39(3), pp. 369-384 (Japanese), pp. 1-30 (English Translation).

Giovambattista De Sarro et al., "GYKI 52466 and Related 2,3-Benzodiazepines as Anticonvulsant Agents in DBA/2 Mice", European Journal of Pharmacology 294 (1995), pp. 411-422.

T. Seppälä, "Tofisopam, A Novel 3,4-Benzodiazepine: Multiple-Dose Effects on Psychomotor Skills and Memory. Comparison with Diazepam and Interactions with Ethanol", Psychopharmacology 69, (1980), pp. 209-218.

Veijo Saano et al., "Tofizopam Modulates the Affinity of Benzodiazepine Receptors in the Rat Brain", Pharmacology Biochemistry & Behavior, vol. 17, (1982), pp. 367-369.

A. Pakkanen et al., "Comparative Study of the Clinical Effects of Tofizopam, Nitrazepam and Placebo as Oral Premedication", British Journal of Anaesthesics, pp. 1009-1012.

V. Saano et al., "Tofizopam Enhances the Action of Diazepam Against Tremor and Convulsions", Medical Biology 61: (1983), pp. 49-53.

V. Saano et al., "Tofizopam Selectively Increases the Action of Anticonvulsants", Medical Biology, 64 (1986), pp. 201-206.

István Tarnawa et al., "Structure-Activity Relationships of 2,3-Benzodiazepine Compounds with Glutamate Antagonistic Action", Bioorganic & Medical Chemistry Letters, vol. 3, No. 1, (1993), pp. 99-104.

K. Yamaguchi et al., PMID: 6136319, Abstract of "Tofisopam, A New 2,3-Benzodiazepine. Inhibition of Changes Induced by Stress Loading and Hypothalamic Stimulation", Can. J. Physiol Pharmaco, vol. 61, (1983), pp. 619-625.

Szegö Judit et al., "Selected Passages From the Clinical-Pharmacological and Clinical Trials of Grandaxin®,"Acta Pharmaceutica Hungarica vol. 63, (1993), pp. 91-98 (Hungarian). pp. 1-10 (English Translation Provided).

L. Petócz et al., The Main Pharmacological Characteristics of Grandaxin (Tofizopam, Egyt-341), Hungarian Medical Journal, vol. 23, No. 4, (1975), pp. 134-138.

Petócz Luijza, "The Pharmacological Effects of Tofizopam (Grandaxin)®", Acta Pharmaceutica Hungarica, vol. 63, (1993), pp. 79-82 (Hungarian. pp. 1-4 (English Translation Provided).

Study of efficacy and safety of Grandaxin tablets for unidentified complaints with digestive system disease. Asano Sadhiro, Orita Yuichi, Kuga Masafumi and Amamor Masanori. Journal of New Remedies & Clinics, 1993, vol. 42, No. 12, pp. 2551-2556. English translation provided.

Clinical Evaluation of Tofisopam (Grandaxin) on Gastro-intestinal Various Unidentified Complaints. Aoyagi Toshio, Kubo Akiyoshi, Sano Masaaki, Kashiwazaki Kazuo, Kojima Toshiya, Nishizato Yoshinori, Koizumi Kazumasa, Yoshioka Masahiro and Miyake Shozo. Japanese Pharmacology & Therapeutics, 1992, vol. 20, No. 2, pp. 657-667. English translation provided.

From actual practice of diagnosis and treatment. Clinical effect of tofisopam (Grandaxin) on unidentified complaints of digestive system. Kitano Atsuo, Okabe Hiroshi, Nakamura Shiro, Obata Akishige, Oshitani Nobuhide, Hioki Masato, Matsumoto Takayuki, Okawa Kiyotaka and Kobaysashi Junzo. Journal of New Remedies & Clinics, 1988, vol. 37, No. 9, pp. 1735-1739. English translation provided.

Effect of Tofisopam (Grandaxin) on irritable colon and cardiac neurosis. Hanajima H. Journal: Yakuri to chiryo. (Japanese pharmacology and therapeutics), 1987, vol. 15. No. 15, pp. 307-217. English translation provided.

Milena Rizzo, "Chromatographic Separation of 2,3-Benzodiazepines", Journal of Chromatography B, 747 (2000), pp. 203-216.

Miklos Simonyi et al, "Stereoselective Binding of a 2,3-Benzodiazepine to Human Serum Albumin", Biochemical Pharmacology, vol. 32, No. 12, (1983), pp. 1917-1920.

Julia Visy et al., "The Role of Configuration and Conformation in the Binding of 2,3-Benzodiazepines to Human Serum Albumin", Chirality 1 (1989), pp. 271-275.

Sergey V. Kalashnikov et al., "Immunomodulating Effects of Tofizopam (Grandaxin®) and Diazepam in Vitro", Mediators of Inflammation, vol. 11, (2002), pp. 53-59.

Fogassy E. et al., "Studies on the Properties and Structure of Optically Active 1-(3,4-Dimethoxyphenyl)-4-Methyl-5-Ethyl-7,8-Dimethoxy-5H-2,3-Benzodiazepine (Tofizopam)", Studies in Organic Chemistry, vol. 18, (1984), pp. 229-233. CA97:6331(Toke), 1982.

Y. Adachi et al., "Use of tofisopam (Grandaxin®) in autonomic imbalance and irritable bowel syndrome", Igaku to Yakugaku, 1987, 18(5), 1591-94, Japan. (Translation provided.).

T. Aoyagi et al., Yakuri to Chiryo, "Clinical evaluation of tofisopam (grandaxin®) in various unidentified gastrointestinal complaints", 1992, 20(2), 295-305, Japan. (Translation provided.).

S. Asano et al., "Study of the efficacy and safety of grandaxin tablets in vague complaints associated with gastrointestinal conditions", Shinyaku to Rinsho, 1993, 42(12), 95-100, Japan. (Translation provided.).

V.S. Chadwick, et al., "Activation of the mucosal immune system in irritable bowel syndrome", *Gastroenterology,* 2002, 122(7), 1778-83.

S.M. Collins, et al., "The putative role of inflammation in the irritable bowel syndrome", *Gut,* 2001, 49(6), 743-45.

M. Csillag et al., "The treatment of climacteric syndrome with tofizopam (grandaxin)", *Ther Hung,* 1975, 23(4), 164-69.

F. Galdiero, et al., "Effects of Benzodiazepines on Immunodeficiency and Resistance in Mice", *Life Sciences,* vol. 57. No. 26, pp. 2413-2423, 1995.

A. Kato et al., "Clinical report on grandaxin for various unidentified complaints", Yakuri to Chiryo, 1987, 15(8), 163-71, Japan. (Translation provided.).

S. Kishimoto et al., "Clinical effect of grandaxin on dyspeptic patients", Yakuri to Chiryo, 1989, 17(5): 457-64, Japan. (Translation provided.).

A. Kitano et al., "Clinical effect of tofisopam (grandaxin®) on vague gastrointestinal complaints", Shinyaku to Rinsho, 1988, 37(9), 169-73, Japan. (Translation provided.).

M. Kojima et al., "Effects of Tofisopam on Lower Digestive Tract Dysfunction", *Clinical Report,* 1996, 30(5), 989-94. (Translation provided.).

Y. Matsuo, et al., "Effect of Tofisopam on Experimental Ulcers", Yakuri to Chiryo, 1998, 16(8), 157-64. (Translation provided.).

M. Osipenko et al., "Role of grandaxin in the treatment of functional diseases of the gastrointestinal tract.", *Terapevt. Arkhiv,* 2000, 10, 23-27. (Translation provided.).

O. Oyesanmi, et al., "Hematologic Side Effects of Psychotropics", *Psychosomatics,* 199, 40(5), 414-21.

J. Ristelhueber et al., "Utility of a new anxiolytic, tofisopam, in current gastroenterology practice," *Revue Francaise de Gastro-Enterologie,* 1977, 125, 49-52, France. (Translation provided.).

J. Szegó et al., "Selected passages from the clinical-pharmacological and clinical trials of grandaxin", *Acta Pharm. Hung.,* 1993, 63, 91-98, Hungary. (Translation provided.).

H. Takada et al., "Clinical study of grandaxin for unidentified complaints", Yakuri to Chiryo, 1989, 17(3), 381-92, Japan. (Translation provided.).

K. Yoshikawa et al., "Clinical evaluation of grandaxin® (tofisopam) on several skin diseases," *Hifu,* 1993, 35(1), 195-202, Japan. (Translation provided.).

Szekely, et al., "Apparent Antinociceptive and Anti-Inflammatory Effects of GYKI 52466", *The European Journal of Pharmacology,* vol. 336, pp. 143-154, (1997).

* cited by examiner

PHARMACEUTICAL COMPOSITION OF 1-(3,4-DIMETHOXYPHENYL)-4-METHYL-5-ETHYL-7-METHOXY-8-HYDROXY-5H-2,3-BENZODIAZEPINE AND USES THEREOF

CROSS-REFERENCE TO RELATED APPLICATION

This application claims the benefit of copending U.S. Provisional Application Ser. No. 60/430,771, filed Dec. 3, 2002, the entire disclosure of which is herein incorporated by reference.

FIELD OF THE INVENTION

The present invention relates to pharmaceutical compositions comprising 1-(3,4-dimethoxyphenyl)-4-methyl-5-ethyl-7-methoxy-8-hydroxy-5H-2,3-benzodiazepine, and to uses of such compounds in methods of treatment.

BACKGROUND OF THE INVENTION 2,3-Benzodiazepines

Certain 2,3-benzodiazepines have been explored extensively for their potent CNS modulating activity. Compounds such as tofisopam (Grandaxin®)(structure shown below, with the atom numbering system indicated), girisopam, and norisopam have demonstrated substantial anxiolytic and antipsychotic activity.

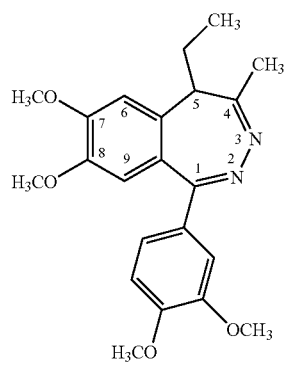

Tofisopam

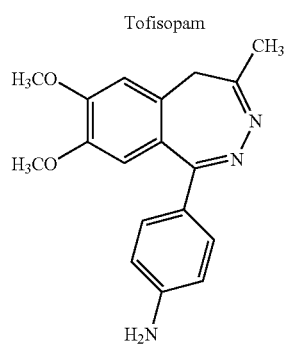

Nerisopam

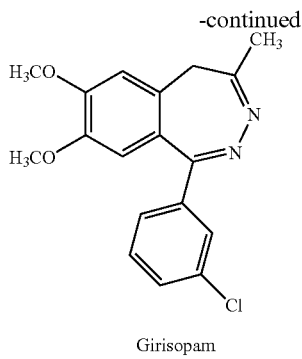

Girisopam

Tofisopam has been shown in humans to have an activity profile that is significantly different from that of widely used 1,4-benzodiazepine (BZ) anxiolytics such as diazepam (Valium®) and chlordiazepepoxide (Librium®). The 1,4-benzodiazepines, in addition to having sedative-hypnotic activity, also possess muscle relaxant and anticonvulsant properties that, though therapeutically useful in some disease states, are nonetheless potentially untoward side effects. Thus the 1,4-benzodiazepines, though safe when administered alone, may be dangerous in combination with other CNS drugs, including alcohol.

Tofisopam, in contrast, is a non-sedative anxiolytic that has no appreciable sedative, muscle relaxant or anticonvulsant properties (Horvath et al., *Progress in Neurobiology*, 60 (2000), 309-342). In clinical studies, tofisopam improved rather than impaired psychomotor performance and showed no interaction with ethanol (Id.). These observations comport with data that show that tofisopam does not interact with central BZ receptors and binds only weakly to peripheral BZ receptors.

Other 2,3-benzodiazepines that are structurally similar to tofisopam have been investigated and shown to have varying activity profiles. For example, GYKI-52466 and GYKI-53655 (structures shown below) act as noncompetitive glutamate antagonists at the AMPA (α-amino-3-hydroxy-5-methyl-4-isoxazolepropionic acid) site, and have demonstrated neuroprotective, muscle relaxant and anticonvulsant activity (Id.). Another group of 2,3-benzodiazepines that have been investigated are represented by the compound GYKI-52895, and show activity as selective dopamine uptake inhibitors with potential use in antidepressant and anti-Parkinsonism therapy.

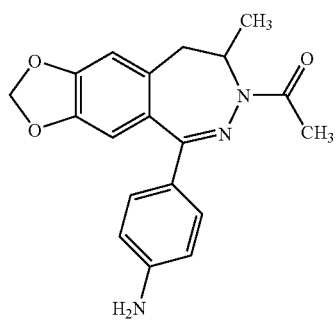

GKY-53655

-continued

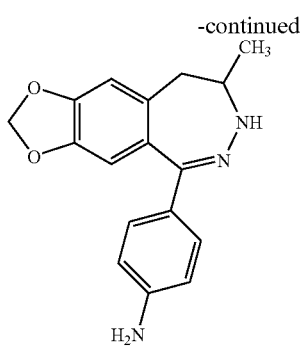

GKY-52895

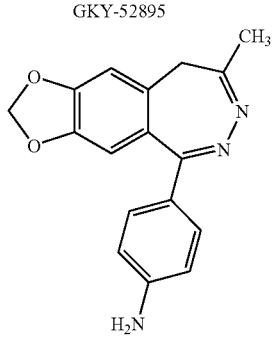

GKY-52466

Tofisopam is a racemic mixture of (R)- and (S)-enantiomers. This is due to the asymmetric carbon, i.e., a carbon with four different groups attached, at the 5-position of the benzodiazepine ring.

The molecular structure and conformational properties of tofisopam have been determined by NMR, CD and x-ray crystallography (Visy et al., *Chirality* 1:271-275 (1989)). The 2,3-diazepine ring exists as two conformers. The major conformers, (+)R and (−)S have the 5-ethyl group in a quasi-equatorial position, while in the minor conformers, (−)R and (+)S, the 5-ethyl group is positioned quasi-axially. Thus, racemic tofisopam may exist as four molecular species, i.e., two enantiomers, each of which exists in two conformations. The sign of the optical rotation is reversed upon inversion of the diazepine ring from one conformer to the other. In crystal form, tofisopam exists only as the major conformations, with dextrorotatory tofisopam being of the (R) absolute configuration. (Toth et al., *J. Heterocyclic Chem.*, 20:709-713 (1983); Fogassy et al., *Bioorganic Heterocycles*, Van der Plas, H. C., Ötvös, L, Simongi, M., eds. Budapest Amsterdam: Akademia; Kiado-Elsevier, 229:233 (1984)).

Differential binding of the (+) and (−) conformers of 2,3-benzodiazepines generally, has been reported for tofisopam in binding studies with human albumin (Simongi et al. *Biochem. Pharm.*, 32(12), 1917-1920, 1983). The (+) and (−) conformers of tofisopam have also been reported as existing in an equilibrium (Zsila et al., *Journal of Liquid Chromatography & Related Technologies*, 22(5), 713-719, 1999; and references therein).

The optically pure (R)-enantiomer of tofisopam (R)-1-(3, 4-dimethoxyphenyl)-4-methyl-5-ethyl-7,8-dimethoxy-5H-2,3-benzodiazepine) has been isolated and shown to possess the nonsedative anxiolytic activity of the racemic mixture. See U.S. Pat. No. 6,080,736; the entire disclosure of which is incorporated herein by reference.

Metabolism of Tofisopam

Tofisopam is metabolized in human, rat, dog, monkey and rabbit to one or more of six major metabolites, depending on the host species:

| Compound # | Compound Name |
| --- | --- |
| 1 | 1-(3,4-dimethoxyphenyl)-4-methyl-5-ethyl-7-hydroxy-8-methoxy-5H-2,3-benzodiazepine |
| 2 | 1-(3,4-dimethoxyphenyl)-4-methyl-5-ethyl-7-methoxy-8-hydroxy-5H-2,3-benzodiazepine |
| 3 | 1-(3-methoxy-4-hydroxyphenyl)-4-methyl-5-ethyl-7,8-dimethoxy-5H-2,3-benzodiazepine |
| 4 | 1-(3-hydroxy-4-methoxyphenyl)-4-methyl-5-ethyl-7,8-dimethoxy-5H-2,3-benzodiazepine |
| 5 | 1-(3-methoxy-4-hydroxyphenyl)-4-methyl-5-ethyl-7-hydroxy-8-methoxy-5H-2,3-benzodiazepine |
| 6 | 1-(3-hydroxy-4-methoxyphenyl)-4-methyl-5-ethyl-7-hydroxy-8-methoxy-5H-2,3-benzodiazepine |

See Tomori et al., *Journal of Chromatography*, 241 (1982), p. 89-99.

Of the compounds named above, Compounds 1, 3 and 5 have been identified as metabolites in humans. These compounds have been synthesized and tested in certain pharmacological assays. C. Ito, "Behavioral Pharmacological Study on the Structure Activity Relationship of Benzodiazepine Derivatives: With Particular Reference to the Activity of 2,3-Benzodiazepine," *J. Tokyo Med. College*, 39:369-384 (1981). In an assay of inhibition of aggression in mice, Compound 1 and 3 showed 0% inhibition of aggression and Compound 5 showed a 28.6% inhibition of aggression. In an assay of muricide (mouse killing behavior) in rats, Compound 3 exhibited 0% inhibition of muricide while Compounds 1 and 5 each exhibited a 20% inhibition of muricide. In assays testing for anti-noradrenergic effects, Compound 1 exhibited no effect, while Compounds 3 and 5 demonstrated measurable activity.

Compounds 1, 3, 5 and 6 are also disclosed in U.S. Pat. No. 4,322,346, the entire disclosure of which is incorporated herein by reference. Compound 3 is reported therein to demonstrate narcosis-potentiating activity in mice.

Leukotriene $B_4$ ($LTB_4$)

Leukotrienes, along with prostaglandins and thromboxanes, are products of arachidonic acid metabolism. $LTB_4$ is produced by leukocytes, particularly macrophage and monocytes upon activation by immune complexes, phagocytosis or other stimuli. $LTB_4$ is a potent chemotactic agent that stimulates neutrophil and macrophage migration (chemotaxis) to sites of inflammation. The structure of $LTB_4$ is shown below.

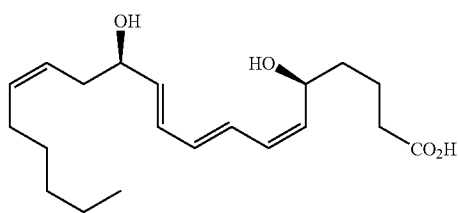

The known pathophysiological responses of $LTB_4$ include: induction of potent neutrophil chemotactic activity, promotion of adhesion of polymorphonuclear leukocytes (PMN) to vasculature, increase in vascular permeability, stimulation of the release of lysosomal enzymes, by PMN. The pro-inflammatory action of $LTB_4$ has been demonstrated in vivo, wherein topical $LTB_4$ on human skin promotes the infiltration of PMN and other inflammatory cells. Intradermal injection of $LTB_4$ induces accumulation of neutrophils at the injection site. Intravenous injection of $LTB_4$ causes rapid but transient neutropenia (Kingsbury et al., *J. Med. Chem.*, 1993, 36, 3308-3320; and references cited therein).

In addition, the presence of physiologically relevant $LTB_4$ concentration at inflammatory sites has been associated with, for example, disease states such as psoriasis, asthma and active gout; in colonic mucosa associated with inflammatory bowel disease; in synovial fluid from patients with active rheumatoid arthritis; and in reperfusion injury. All of these observations together support the involvement of $LTB_4$ in human inflammatory disease (Kingsbury et al, and Griffeths et al., *Proc. Natl. Acad. Sci.* Vol. 92, pp517-521, January 1995; and references cited therein.).

Inflammatory Disorders

Crohn's disease and ulcerative colitis, collectively referred to as inflammatory bowel disease (IBD), are chronic recurrent inflammatory diseases of unclear etiology, affecting the small intestine and colon. Inflammatory bowel disease (IBD) can involve either or both the small and large bowel. These disorders fall into the category of "idiopathic" inflammatory bowel disease because the etiology for them is unknown.

Pathologic findings are generally not specific, although they may suggest a particular form of IBD. "Active" IBD is characterized by acute inflammation. "Chronic" IBD is characterized by architectural changes of crypt distortion and scarring. The term "crypt" refers to a deep pit that protrudes down into the connective tissue surrounding the small intestine. Crypt abscesses (active IBD characterized by the presence of neutrophils in crypt lumens) can occur in many forms of IBD, not just ulcerative colitis. Under normal conditions the epithelium at the base of the crypt is the site of stem cell proliferation and the differentiated cells move upwards and are shed 3-5 days later at the tips of the villi. This normal process, necessary for proper bowel function, is interrupted by IBD Ulcerative colitis (UC) involves the colon as a diffuse mucosal disease with distal predominance. The rectum is virtually always involved, and additional portions of colon may be involved extending proximally from the rectum in a continuous pattern. Most often ulcerative colitis occurs in young people 15 to 40 years of age. Ulcerative colitis occurs only in the inner lining of the colon (large intestine) or rectum. When it is localized in the rectum, it is called "proctitis."

Crohn's Disease is a chronic inflammatory disease that has periods of remission (time when person feels well) and relapse (when a person feels ill). Crohn's disease is an inflammation and ulceration process that occurs in the deep layers of the intestinal wall. The most common areas affected are the lower part of the small intestine, called the ileum, and the first part of the colon. This type of Crohn's disease is called ileocolitis. Crohn's disease can infrequently affect any part of the upper gastrointestinal tract. Aphthous ulcers, which are similar to cold sores, are common. Ulcers can also occur in the esophagus, stomach and duodenum.

Therapy for IBD has historically included administration of corticosteroids. However drawbacks of long term corticosteroid therapy include masking (or induction) of intestinal perforation, osteonecrosis and metabolic bone disease. Additional problems relate to development of corticosteroid dependency (Habnauer, New England Journal of Medicine, 334(13), p 841-848, 1996). Aminosalicylates such as sulfasalazine and mesalamine have been used to treat mild or moderately active ulcerative colitis and Crohn's Disease, and to maintain remission (Id at 843). Immunomodulatory drugs such as azathioprine and mercaptopurine have been used in long term treatment for patients with IBD. Common complications with both of these drugs include pancreatitis, which occurs with an incidence of 3-15% of patients, and bone marrow suppression, which requires regular monitoring. More potent immunosuppressive drugs such as cyclosporine and methotrexate have been employed, but toxicity of these drugs limits their use to specific situations of refractory disease states. Other therapeutic approaches include antibiotic therapy and nutritional therapy. Often, therapy involves a combination of the above-described drug therapies in addition to surgical resection of the bowel.

There is no cure for IBD. Ultimately, the chronic and progressive nature of IBD demands a long-term treatment that maximizes the local antiinflammatory effect while minimizing the global systemic effect on the immune system.

Chronic inflammatory disorders such as Crohn's Disease typically demonstrate periods of remission between intervals when the inflammatory is active and requires acute treatment. This is an example of a circumstance wherein it is known beforehand that an individual will develop, or is likely to develop an inflammatory disorder.

Another chronic inflammatory condition believed to be mediated by $LTB_4$ is psoriasis. Psoriasis is a chronic, recurrent, papulosquamous plaque on areas of trauma such as the elbow, knee or scalp, though it may appear elsewhere on the skin. Psoriasis may coexist with *lupus erythematosis* in some individuals. Current treatments include topical administration of psoralens. "Psoralens" refers to a group of substances found in many different plants, especially *psoralea corylifolia*. Psoralens interact with nucleic acids and are also used as research tools. Psoriasis is also treated by long-wave ultraviolet radiation. Neither treatment cures or prevents recurrence of psoriasis symptoms.

Another chronic inflammatory disorder believed to be mediated by $LTB_4$ is rheumatoid arthritis, which is an autoimmune disease of the joints. Rheumatoid arthritis is characterized by the following criteria 1-7, wherein criteria 1-4 are present for more than 6 weeks: (1) morning stiffness in and around joints lasting at least one hour before maximum improvement; (2) soft tissue swelling (arthritis) of three or more joints observed by a physician; (3) swelling (arthritis) of the proximal interphalangeal, metacarpal phalangeal, or wrist joints; (4) symmetric swelling; (5) rheumatoid nodules, i.e., a granulomatous lesion characterized by central necrosis encircled by a palisade of monocytes and an exterior mantle of lymphocytic infiltrate. These lesions present as subcutaneous nodules, especially at pressure points such as the elbow in individuals with rheumatoid arthritis or other rheumatoid disorders; (6) presence of rheumatoid factors, i.e., an autoantibody in the serum of individuals with rheumatoid arthritis; and (7) roentgenographic erosions, i.e., joint lesions visible on an X-ray.

Rheumatoid arthritis is a chronic disorder for which there is no known cure. The major goals of treatment of rheumatoid arthritis are to reduce pain and discomfort, prevent deformities and loss of joint function, and maintain a productive and active life. Inflammation must be suppressed and mechanical and structural abnormalities corrected or compensated by assistive devices. Treatment options include reduction of joint stress, physical and occupational therapy, drug therapy, and surgical intervention.

There are three general classes of drugs commonly used in the treatment of rheumatoid arthritis: non-steroidal anti-inflammatory agents (NSAID's), corticosteroids, and remittive agents or disease modifying anti-rheumatic drugs (DMARD's). NSAID's and corticosteroids have a short onset of action while DMARD's can take several weeks or months to demonstrate a clinical effect. DMARD's include leflunomide (Arava™), etanercept (Enbrel™), infliximab (Remicade™), antimalarials, methotrexate, gold salts, sulfasalazine, d-penicillamine, cyclosporin A, cyclophosphamide and azathioprine. Because cartilage damage and bony erosions frequently occur within the first two years, rheumatologists now move more aggressively to a DMARD agent.

Treatment of rheumatoid arthritis by chronic administration of a corticosteroid involves the same side effect profile as discussed regarding IBD above. Chronic administration of NSAID's also produces side effects. The most common toxicity of NSAID's is gastrointestinal disturbance. Because prostaglandins play a role in the regulation of renal blood flow and maintenance of glomerular filtration, NSAID's can impair renal function in certain patients. Weight gain and cushingoid appearance is a frequent problem and source of patient complaints. Recent studies have raised concern over the increased cardiovascular risk and accelerated osteoporosis associated with low dose prednisone particularly at doses above 10 mg daily.

Gout is another inflammatory disorder believed to be mediated by $LTB_4$. Gout is characterized by a disturbance of uric-acid metabolism occurring chiefly in males. Gout is characterized by painful inflammation of the joints, especially of the feet and hands, and arthritic attacks resulting from elevated levels of uric acid in the blood and the deposition of urate crystals around the joints. The condition can become chronic and result in deformity.

Gout can present another circumstance wherein it is known beforehand that an individual will or is likely to develop an inflammatory disorder. In the instance of patients undergoing radiotherapy or chemotherapy, the individual may experience a dramatic rise in serum uric acid levels associated with lysis of the tumor mass. Such large increases in uric acid can deposit urate crystals in synovial fluid of joints thereby causing the inflammatory disorder, gout. When such a rise in serum uric acid levels is known to be likely, prophylaxis with an $LTB_4$ antagonist can act to prevent the inflammatory condition of gout.

Radiation-induced gastrointestinal inflammation is another inflammatory disorder believed to be mediated by $LTB_4$. Radiation works by damaging cancer cells, but unfortunately can damage non-diseased tissue as well, causing a typical inflammatory reaction in response. Therapeutic radiation is thus generally applied to a defined area of the subject's body which contains abnormal proliferative tissue in order to maximize the dose absorbed by the abnormal tissue and minimize the dose absorbed by the nearby normal tissue. However, it is difficult (if not impossible) to selectively administer therapeutic ionizing radiation to the abnormal tissue. Thus, normal tissue proximate to the abnormal tissue is also exposed to potentially damaging doses of ionizing radiation throughout the course of treatment. Moreover, some treatments that require exposure of the subject's entire body to the radiation, in a procedure called "total body irradiation", or "TBI." The efficacy of radiotherapeutic techniques in destroying abnormal proliferative cells is therefore necessarily balanced by the associated cytotoxic effects on nearby normal cells.

After or during a course of radiotherapy, $LTB_4$-mediated inflammatory processes may be triggered, causing damage to the bowel, and leading to sloughing of the cells of the inner lining of the GI tract. Radiation-induced gastrointestinal inflammation can present another circumstance wherein it is known beforehand that an individual will or is likely to develop an inflammatory disorder. In the instance of patients undergoing radiotherapy, the inflammation, damage and sloughing of the gastrointestinal tract is a predictable side effect of the radiotherapy.

New antiinflammatory agents are needed which are useful in the treatment of inflammatory disorders such as IBD, rheumatoid arthritis, gout, psoriasis and radiation-induced gastrointestinal inflammation. In particular, agents are needed that are appropriate for chronic long-term use in treatment. In addition, agents are needed that are useful in the prevention of $LTB_4$-mediated inflammatory disorders that occur secondary to observable events such as ionizing radiation therapy.

Thromboxane $A_2$

Thromboxane $A_2$ ($TXA_2$), like $LTB_4$, is a product of the arachidonic acid metabolic pathway. $TXA_2$ induces a variety of differential cellular responses including platelet aggregation, contraction of vascular and bronchial smooth muscle cells (SMC), potentiation of hypertrophic and mitogenic responses in vascular SMC and endothelial cells.

$TXA_2$ is considered to be an important mediator of asthma because it can induce contraction of airway smooth muscle, and because it has been implicated in airway hyperresponsiveness in animal models wherein increased airway reactivity was induced by allergens, platelet-activating factor (PAF), $LTC_4$, $LTD_4$, $LTB_4$, bradykinin, endothelin, endotoxin and ozone. (See J. Dogne et al., *Expert Opin. Investig. Drugs* (2002), 11(2), and references cited therein, the entire disclosures of which are incorporated herein by reference.)

$TXA_2$ has also been implicated in the pathophysiology of radicular pain induced by hemeated nucleus pulposis. A study in a rat model examined the role of $TXA_2$ (and $LTB_4$) in the hyperalgesia induced by application of nucleus pulposus to the lumbar nerve root in the rat. A $TXA_2$ synthetase inhibitor, injected into the epidural space, decreased mechanical hyperalgesia at both three and seven days after epidural injection. There were no significant differences in sensitivity to noxious thermal stimuli following application of the nucleus pulposus or an epidural injection. Epidural injection of $TXA_2$ synthetase inhibitor may attenuate the painful radiculopathy due to lumbar disc herniation.

$TXA_2$ has further been implicated as an in vivo mediator of fibroblast growth factor (FGF)-stimulated angiogenesis. See, T. Daniel et al., *Cancer Research*, 59, 4574-4577, Sep. 15, 1999, the entire disclosure of which is incorporated herein by reference. Thromboxane synthase inhibitors have further been shown to inhibit metastasis of lung carcinoma in a mouse model, thus demonstrating the involvement of $TXA_2$ in angiogenesis and tumor metastasis. See, D. Nie et al., *Biochem. Biophys. Res. Commun.*, 2000, 267(1), p. 245-251, the entire disclosure of which is incorporated herein by reference.

$TXA_2$ is also believed to possess anticoagulant activity. See Schenk et al., "Antiplatelet and anticoagulant effects of "HN-11 500," a selective thromboxane receptor antagonist," *Thromb. Res.* 2001 Jul. 15; 103(2):79-91.

Anticoagulant has potential therapeutic value in chronic inflammation according to a model associating chronic inflammatory disorders with a coagulation protein defect is termed immune system activation of coagulation (ISAC). The model proposes that a majority of individuals diagnosed with certain chronic inflammatory illnesses may, based on clinical criteria, be potentially defined as or involve AntiPhospholipid Antibody Syndrome (APS)-with the endothelial cell (EC) as the disease target. These patients have a hypercoagulable, state demonstrated by increased markers of coagulation activation and increased blood viscosity due to the generation of Soluble Fibrin Monomer (SFM). The CFS/FM process and related processes may be triggered by a variety of pathogens (CMV, HHV6, Mycoplasma, Chlamydia pneumonia, etc.), or some vaccines, resulting in pathogen-mediated immune activation that induces antibodies which cross react with EC protective proteins B2GPI & Annexin V. These antibodies dislodge the protective proteins from EC surfaces, exposing PhosphatidylSerine (PS) on the EC surfaces in capillary beds.

Pathogens induce inflammatory responses which include cytokine modulation of EC to down regulate the antithrombotic environment (ThromboModulin, tPA) in favor of prothrombotic expression of Tissue Factor (TF). TF and PS exposure allows binding of the coagulation tenase and prothombinase complexes to EC surfaces. This results in thrombin generation leading to SFM formation. SFM dimerizes easily, increasing blood viscosity and precipitating out on EC surfaces as fibrin(oid) deposition, creating local ischemia and pathology, blocking nutrient and oxygen delivery in the microcirculation. A blood clot does not form because there is not enough of a thrombin burst to activate Factor XIII to cross link the fibrin into a clot.

A hereditary defect in a coagulation regulatory protein; such as protein C, protein S. Factor $V^L$, prothrombin gene mutation, Heparin Cofactor II, tPA, $PAI_{-1}$, Lp(a), or elevated Factor II, X, XII, or homacysteine is predispositional in greater than 75% of patients. Because this hypercoagulability does not result in an immediate thrombosis (100% occlusion), but rather in fibrin deposition (50-95%), it has been suggested that an appropriate name for this antiphospholipid antibody process would be Immune System Activation of Coagulation (ISAC) syndrome.

The ISAC model provides an explanation for the therapeutic benefits reported with low dose anticoagulant therapy (heparin or warfarin) in some of these patients. Diagnoses with published associations include: Chronic Fatigue. Syndrome/Fibromyalgia (CFS/FM), Infertility (Recurrent Fetal Loss and Fetal Wastage Syndromes), Osteonecrosis of the Jaw, Multiple Sclerosis (MS), Depression and Autism. Diagnoses under investigation include: Crohn's Disease and Inflammatory Bowel Disease (IBD), Late Lyme Disease, Sjogren's Syndrome (SS), Transient Ischemic Attack (TIA), Attention Deficit Disorder (ADD) and Parkinson's Disease. See Berg et al., "Chronic Fatigue Syndrome &/or Fibromyalgia as a variation of antiphospholipid antibody syndrome (APS): An explanatory model and approach to laboratory diagnosis," *Blood Coagulation and Fibrinolysis*, 1999, 10:435-438.

New $TXA_2$ agents are needed which may be useful in the treatment of $TXA_2$-mediated disorders such as asthma, pain, tumors in which angiogenesis associated with the tumor is mediated by $TXA_2$, and in chronic inflammatory illnesses such as, for example Chronic Fatigue Syndrome/Fibromyalgia, IBD, Crohn's Disease, late Lyme disease and IBD.

Adenosine

Adenosine is a multi-purpose signal molecule that regulates a variety of cellular functions and is released under conditions of physiological stress. The actions of adenosine are mediated through four receptor subtypes ($A_1$, $A_{2A}$, $A_{2B}$ and $A_3$).

Adenosine acts at the $A_1$ receptor subtype to cause decreases in heart rate, force of contraction, and responsiveness to adrenaline, and at the $A_{2A}$ receptor subtype to cause dilation of coronary arteries to enhance blood flow to the heart. In the central nervous system (CNS), adenosine, released during episodes of epilepsy or as a consequence of hypoxia or stroke, acts at the $A_1$ receptor subtype to exert a neuroprotective action by decreasing electrical excitability, inhibiting the release of excitatory amino acids (EAA) and acts at the $A_{2A}$ receptor subtype to increase cerebral blood flow.

In the kidney, $A_1$ receptors located on preglomerular vessels and in the tubule are involved in the regulation of glomerular filtration. Whole body fluid balance is strongly dependent on the ability of the kidney to maintain stable glomerular filtration. Several antagonists to $A_1$ receptors have been developed. These agents generate excess fluid (diuresis) and sodium (natriuresis) excretion in control animals and animal models of fluid retention, as well as in normal and oedematous humans. In both animals and humans, these effects are generally achieved without major changes in glomerular filtration. Animal studies have confirmed the location of $A_1$ receptors in relevant tissue sites in the kidney. More highly selective antagonists for $A_1$ receptors are regularly developed, improving their use in fluid retaining disorders. See Welch W J, "Adenosine type 1 receptor antagonists in fluid retaining disorders," *Expert Opin Investig Drugs* 2002 November; 11(11):1553-62.

Adenosine, whether endogenously released or added exogenously, is a potent antiinflammatory agent. Adenosine mediates its antiinflammatory effects via interaction with specific receptors ($A_1$, $A_{2a}$, $A_{2b}$ and $A_3$) on the surface of inflammatory cells. Receptor-specific analogs of adenosine have been shown to increase the rate at which wounds heal. Am J Pathol 2002 June; 160(6):2009-18.

Adenosine promotes wound healing and mediates angiogenesis in response to tissue injury via occupancy of $A_{2A}$ receptors. See Montesinos et al., "Adenosine promotes wound healing and mediates angiogenesis in response to tissue injury via occupancy of $A_{2A}$ receptors," *Am. J. Pathol.* 2002 June; 160(6):2009-18, and Victor-Vega et al., "Adenosine $A_{2A}$ receptor agonists promote more rapid wound healing than recombinant human platelet-derived growth factor (Becaplermin gel)," *Inflammation* 2002 February; 26(1):19-24.

Adenosine is believed to mediate gastrointestinal relaxation through two different inhibitory receptor subtypes; $A_1$ receptors on the enteric neuron and $A_{2B}$ receptor on the smooth muscle in the guinea-pig distal colon. See Kadowaki et al., "Molecular identification and pharmacological characterization of adenosine receptors in the guinea-pig colon," *Br. J. Pharmacol.* 2000 March; 129(5):871-6.

Adenosine binds to the receptor subtypes and activates the receptors to produce G proteins. G proteins themselves can either stimulate ($G_s$) or inhibit ($G_i$) the enzyme adenylate cyclase so as to generate or prevent the manufacture of cyclic AMP. In addition, G coupled proteins can open potassium channels in cardiac tissue, resulting in depression of cardiac electrical activity. The following Table enumerates adenosine activity on different tissues.

TABLE 1

Effect of Adenosine Receptor Activation

| Receptor Subtype | Heart | CNS | Kidney | Other |
|---|---|---|---|---|
| $A_1$ | Heart Rhythm-decrease in heart rate, force of atrial contraction, and responsiveness to adrenaline | Wakefulness-decrease in electrical excitability and inhibition of excitatory amino acid (EAA) release | Anti-diuresis | Anti-lipolytic insulin enhancer Antihypertensive Wound healing Hair growth |

TABLE 1-continued

Effect of Adenosine Receptor Activation

| Receptor Subtype | Heart | CNS | Kidney | Other |
|---|---|---|---|---|
| $A_{2A}$ | Regulates blood vessel tone-dilation of the coronary arteries supplying blood to the heart muscle | Anti-Inflammatory-cerebral blood flow increase | | Wound healing |
| $A_{2B}$ | | | | Allergic Responses GI Tract Relaxation Anti-Inflammatory |
| $A_3$ | Cardio-protective | | | Allergic Responses |

Adenosine helps protect the heart muscle from damage when myocardial ischemia occurs. See Maddock H L et al., "Adenosine $A_3$ receptor activation protects the myocardium from reperfusion/reoxygenation injury," *Am. J. Physiol. Heart. Circ. Physiol.* 2002 October; 283(4):H1307-13. When this happens, adenosine is released in the heart vessels and myocardium and acts to: enlarge vessels to increase blood and oxygen supply; improve energy supply for the myocardium and decrease energy needs; produces angina pectoris, the signature warning symptom of myocardial ischemia. Adenosine has a depressant effect on sinoatrial node activity and thus exerts an arrythmogenic effect. See Belhassen B., "Adenosine triphosphate in cardiac arrhythmias: from therapeutic to diagnostic use," *Pacing Clin. Electrophysiol.* 2002 January; 25(1):98-102; and Meester, B J et al., "Pharmacological classification of adenosine receptors in the sinoatrial and atrioventricular nodes of the guinea-pig," *Br. J. Pharmacol.* 1998 June; 124(4):685-92. This makes adenosine effective in treating tachyarrhythmias involving the sinoatrial node. Ongoing research suggests that adenosine will be important in protecting the heart during open-heart surgery. See Safran N et al., "Cardioprotective effects of adenosine $A_1$ and $A_3$ receptor activation during hypoxia in isolated rat cardiac myocytes," *Mol. Cell. Biochem.* 2001 January; 217(1-2): 143-52.

Adenosine signaling has also been implicated to play a role in various types of lung inflammation including those seen in asthma and chronic obstructive pulmonary disease (COPD). Asthma is an inflammatory disease of the lung characterized by acute nonspecific airway hyperreactivity in association with chronic pulmonary inflammation. The disease effects approximately 10% of children and 6% of adults in the United States alone, and its incidence is increasing at an alarming rate. COPD is a progressive disease process that most commonly results from smoking. COPD is characterized by difficulty breathing, wheezing and a chronic cough.

The major observations are that adenosine levels are elevated in the lungs of asthmatics, inhaled adenosine causes bronchoconstriction in asthmatics but not normal subjects, the pattern of adenosine receptor expression is altered in the lung of asthmatics, and theophylline, an adenosine receptor antagonist, has well recognized benefits in the treatment of asthma. In addition to this clinical evidence, there are many in vitro studies in both human and animal cells that implicate adenosine as a modulator of inflammatory processes that are central to asthma. Most notable are adenosine's ability to enhance mediator release from mast cells, and to influence eosinophil survival and chemotaxis. However, despite these lines of evidence, a clear implication for adenosine signaling in asthma, and the cell types and mechanisms involved, are unclear.

Adenosine is also a modulator of dopamine mediated motor responses. A new therapeutic approach to the treatment of Parkinson's disease is to synergistically modulate the effects of dopamine agonists in order to decrease the dosages of drugs used. Recent research suggests a potential positive role of $A_{2A}$ antagonists in Parkinson's disease. See "Adenosine Receptors and Parkinson's Disease," Hiroshi Kase (Editor), Peter J. Richardson (Editor), Peter Jenner (Editor), Academic Press; ISBN: 0124004059; 1st edition (Jan. 15, 2000). The current chronic treatment of Parkinson's disease with L-DOPA causes important complication as motor fluctuations and dyskinesias, thus new agents are needed that adequately treat Parkinson's Disease without concomitant dyskinetic side effects.

Adenosine has also been investigated as a potential mediator in regeneration of hematopoietic progenitor cells in mouse models of severe myelosuppression. In the study, drugs that elevate extracellular adenosine were shown to modulate regeneration from severe myelosuppression resulting from combined exposure of the animals to ionizing radiation and carboplatin. In the model, elevation of extracellular adenosine was induced by joint administration of dipyridamole (DP), a drug inhibiting the cellular uptake of adenosine, and adenosine monophosphate (AMP), serving as an adenosine prodrug. The test drugs were administered in a 4-day treatment regimen starting on day 3 after induction of myelosuppression. (The drug regimen was tested with and without co-administration of granulocyte colony stimulating factor.) The effects of the drug treatments on progenitor cells were reflected in the peripheral blood in later time intervals of days 15 and 20 after induction of myelosuppression, especially as significantly elevated numbers of granulocytes and less pronounced elevation of lymphocytes and erythrocytes. The results substantiate the potential of drugs elevating extracellular adenosine for clinical utilization in myelosuppressive states, e.g. those accompanying oncological radio- and chemotherapy.

New agents are needed that selectively act at specific adenosine receptors and may thus which be useful in the treatment of adenosine-mediated disorders. Such disorders include, for example, neurological disorders such as epilepsy, stroke and cerebral ischemia; heart failure; and regeneration of hematopoietic cells associated with myelosuppression caused by ionizing radiation therapy of cancer chemotherapy.

SUMMARY OF THE INVENTION

According to one embodiment of the invention, there is provided a pharmaceutical composition comprising a pharmaceutically acceptable carrier and the compound 1-(3,4-dimethoxyphenyl)-4-methyl-5-ethyl-7-methoxy-8-hydroxy-5H-2,3-benzodiazepine, or a pharmaceutically acceptable salt thereof. The compound has the formula:

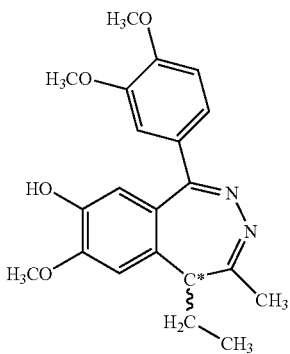

wherein C* is a chiral carbon and the bond designated by ~~~ indicates that the absolute conformation about C* may be either (R) or (S);

According to other embodiments, various therapeutic methods are provided. For each such therapeutic method described in the herein Summary of Invention, the term, "1-(3,4-dimethoxyphenyl)-4-methyl-5-ethyl-7-methoxy-8-hydroxy-5H-2,3-benzodiazepine" is meant to also extend to pharmaceutically acceptable salts thereof.

According to one embodiment of the invention, a method of treating an inflammatory disorder mediated by $LTB_4$ is provided comprising administering to an individual in need of such treatment a therapeutically effective amount of 1-(3,4-dimethoxyphenyl)-4-methyl-5-ethyl-7-methoxy-8-hydroxy-5H-2,3-benzodiazepine.

According to another embodiment of the invention, a method of preventing or delaying the onset of an inflammatory disorder mediated by $LTB_4$ is provided comprising administering to an individual who is at risk of developing such an inflammatory disorder, a therapeutically effective amount of 1-(3,4-dimethoxyphenyl)-4-methyl-5-ethyl-7-methoxy-8-hydroxy-5H-2,3-benzodiazepine.

According to another embodiment of the invention a method of treating a disorder mediated by $TXA_2$, is provided, comprising administering to an individual in need of such treatment a therapeutically effective amount of 1-(3,4-dimethoxyphenyl)-4-methyl-5-ethyl-7-methoxy-8-hydroxy-5H-2,3-benzodiazepine.

According to another embodiment of the invention a method of preventing or delaying the onset of a disorder mediated by $TXA_2$, is provided, comprising administering to an individual in need of such treatment a therapeutically effective amount of 1-(3,4-dimethoxyphenyl)-4-methyl-5-ethyl-7-methoxy-8-hydroxy-5H-2,3-benzodiazepine.

According to another embodiment of the invention, a method of treating a disorder mediated by adenosine is provided, comprising administering to an individual in need of such treatment a therapeutically effective amount of 1-(3,4-dimethoxyphenyl)-4-methyl-5-ethyl-7-methoxy-8-hydroxy-5H-2,3-benzodiazepine.

According to another embodiment of the invention, there is provided a method of preventing, reducing or delaying the onset of adenosine mediated myelosuppression associated with cytotoxic chemotherapy or ionizing radiation therapy in an individual who is at risk of developing such myelosuppression due to the present or imminent administration to said individual of cytotoxic chemotherapy or ionizing radiation therapy, said method comprising administering to said individual a therapeutically effective amount of the composition according to claim 1.

The invention also relates to the use in medicine of 1-(3,4-dimethoxyphenyl)-4-methyl-5-ethyl-7-methoxy-8-hydroxy-5H-2,3-benzodiazepine, the (R)- or (S)-enantiomers thereof, or pharmaceutically acceptable salts thereof.

According to another aspect of the invention, the aforesaid compounds are used in the preparation of medicaments for (i) treating an $LTB_4$-mediated inflammatory disorder, or for preventing or delaying the onset of such a disorder; (ii) treating a $TXA_2$-mediated disorder or for preventing or delaying the onset of such a disorder; (iii) treating an adenosine-mediated disorder and (iv) preventing or delaying the onset of adenosine-mediated myelosuppression associated with cytotoxic chemotherapy or ionizing radiation therapy.

In the compositions and methods discussed herein, the compound may comprise racemic-1-(3,4-dimethoxyphenyl)-4-methyl-5-ethyl-7-methoxy-8-hydroxy-5H-2,3-benzodiazepine, or the substantially isolated (R)- or (S)-enantiomer. Preferably, the administered compound is in the form of a single enantiomer of 1-(3,4-dimethoxyphenyl)-4-methyl-5-ethyl-7-methoxy-8-hydroxy-5H-2,3-benzodiazepine, which comprises 80% or more by weight of the total weight of the compound.

In one embodiment, there is provided a pharmaceutical composition comprising (R)-1-(3,4-dimethoxyphenyl)-4-methyl-5-ethyl-7-methoxy-8-hydroxy-5H-2,3-benzodiazepine substantially free of the (S)-enantiomer In another embodiment, there is provided pharmaceutical composition comprising (S)-1-(3,4-dimethoxyphenyl)-4-methyl-5-ethyl-7-methoxy-8-hydroxy-5H-2,3-benzodiazepine substantially free of the (R)-enantiomer.

More preferably compounds used in the compositions and methods of the present invention have a composition that is 85% by weight or greater of the desired enantiomer, and 15% by weight, or less, of the other enantiomer. Still more preferably, compounds used in compositions and methods of the present invention have a composition that is 90% by weight or greater of the desired enantiomer and 10% by weight, or less, of the other enantiomer. Even more preferably, compounds used in compositions and methods of the present invention have a composition that is 95% by weight or greater of the desired enantiomer and 5% by weight, or less, of the other enantiomer. Most preferably, compounds used in the compositions and methods of the present invention have a composition that is 99% by weight or greater of the desired enantiomer and 1% by weight, or less, of the other enantiomer.

According to one particular embodiment, the compound comprises 90% or more by weight of the (R)-enantiomer.

Definitions

The terms "inflammation" and "inflammatory response" refer to a defense reaction of living tissue to injury. The response serves to contain and to repair the injury.

An "inflammatory disorder mediated by $LTB_4$" or a "$LTB_4$-mediated disorder", means to a disorder resulting from an inflammatory response wherein $LTB_4$ mediation is implicated as a factor by observation of $LTB_4$ presence at the site of the inflammation or by other evidence that $LTB_4$ is involved in the etiology or progression of the inflammatory disorder.

The term "$TXA_2$-mediated disorder" means a disorder wherein $TXA_2$ mediation is implicated as a factor in the etiology or progression of the disorder or in the mechanisms whereby the disorder negatively affects the organism suffering therefrom.

The term "angiogenesis" means the process of vascularization of a tissue involving the development of new capillary blood vessels. Vascularization of tumors is usually a prelude to more rapid growth and often to metastasis.

The term "asthma" refers to a chronic respiratory disease, often arising from allergies, that is characterized by sudden recurring attacks of labored breathing, chest constriction, and coughing, due to due to a spasmodic contraction of the bronchi.

The term "myelosuppression" refers to a reduction in blood-cell production by the bone marrow. It commonly occurs after chemotherapy or ionizing radiation therapy and may result in anemia, infection, and abnormal bleeding.

The term "cerebral ischemia" refers to a decrease in the blood supply to the brain caused by constriction or obstruction of the blood vessels such as a stroke or a transient ischemic attack (TIA).

The phrase "optically active" refers to a property whereby a material rotates the plane of plane-polarized light. A compound that is optically active is nonsuperimposable on its mirror image. The property of nonsuperimposablity of an object on its mirror image is called chirality.

The property of "chirality" in a molecule may arise from any structural feature that makes the molecule nonsuperimposable on its mirror image. The most common structural feature producing chirality is an asymmetric carbon atom, i.e., a carbon atom having four nonequivalent groups attached thereto.

The term "enantiomer" refers to each of the two nonsuperimposable isomers of a pure compound that is optically active. Single enantiomers are designated according to the Cahn-Ingold-Prelog system, a set of priority rules that rank the four groups attached to an asymmetric carbon. See March, Advanced Organic Chemistry, 4$^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking sequence id A>B>C>D. The lowest ranking atom, D is oriented away from the viewer.

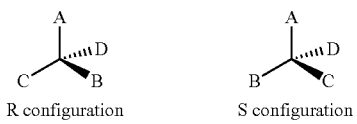

The term "racemate" or the phrase "racemic mixture" refers to a 50-50 mixture of two enantiomers such that the mixture does not rotate plane-polarized light.).

The term "substantially isolated", or "substantially free" of the other enantiomer or the term "resolved" when used to refer to an optically active compound of formula I, means the (R)- and (S)-enantiomers of the compound have been separated such that the composition is 80% or more by weight a single enantiomer.

Thus, by "(R)-1-(3,4-dimethoxyphenyl)-4-methyl-5-ethyl-7-methoxy-8-hydroxy-5H-2,3-benzodiazepine substantially free of the (S)-enantiomer" is meant 1-(3,4-dimethoxyphenyl)-4-methyl-5-ethyl-7-methoxy-8-hydroxy-5H-2,3-benzodiazepine that comprises 80% or more by weight of the (R)-enantiomer and likewise contains 20% or less of the (S)-enantiomer as a contaminant, by weight. Likewise, by "(S)-1-(3,4-dimethoxyphenyl)-4-methyl-5-ethyl-7-methoxy-8-hydroxy-5H-2,3-benzodiazepine substantially free of the (R)-enantiomer" is meant 1-(3,4-dimethoxyphenyl)-4-methyl-5-ethyl-7-methoxy-8-hydroxy-5H-2,3-benzodiazepine that comprises 80% or more by weight of the (S)-enantiomer and likewise contains 20% or less of the (R)-enantiomer as a contaminant, by weight.

The term "effective amount" when used to describe the amount of drug administered to a patient suffering from a $LTB_4$-mediated inflammatory disorder, refers to the amount of amount of 1-(3-hydroxy-4-methoxyphenyl)-4-methyl-5-ethyl-7,8-dimethoxy-5H-2,3-benzodiazepine, or a pharmaceutically acceptable salt thereof that inhibits the inflammatory process, resulting in a therapeutically useful and selective reduction in the symptoms of inflammation.

An "effective amount" of the compound when used to describe the amount of drug administered for the prevention of an $LTB_4$ mediated inflammatory disorder is an amount which prevents or delays the onset of symptoms of an inflammatory disorder in an individual during a time interval coinciding with an increased risk of $LTB_4$-mediated inflammatory disorder.

The term "effective amount" when used to describe therapy to a patient suffering from $TXA_2$-mediated pain, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that inhibits the process whereby pain is generated, thus resulting in a therapeutically useful and selective reduction in the pain sensation.

The term "effective amount" when used to describe the amount of drug administered to a patient suffering from $TXA_2$-mediated angiogenesis in a tumor, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that inhibits the process whereby new blood vessels are generated that associate with the developing tumor, thus resulting in a therapeutically useful and selective reduction rate of tumor development.

The term "effective amount" when used to describe therapy to a patient suffering from $TXA_2$-mediated asthma, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that ameliorates the symptoms of asthma, when administered to a patient suffering therefrom.

The term "effective amount" when used to describe the amount of drug administered to a patient who has suffered a stroke or other cerebral ischemic condition, or who is at elevated risk of suffering a stroke or other cerebral ischemic condition, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that results in a therapeutically useful reduction or elimination of the neuronal cell death associated with such a disorder.

The term "effective amount" when used to describe the amount of drug administered to a patient who has suffered a stroke or other cerebral ischemic condition, or who is at elevated risk of suffering a stroke or other cerebral ischemic condition, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that results in a therapeutically useful reduction or elimination of the neuronal cell death associated with such a disorder.

The term "effective amount" when used to describe the amount of drug administered to a patient suffering from epilepsy, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that results in a therapeutically useful decrease in the frequency, the severity or both of the seizures associated with such a disorder.

The term "epilepsy" refers to any of various neurological disorders characterized by recurring attacks of motor, sensory, or psychic malfunction with or without loss of consciousness and with or without convulsive seizures.

The term "effective amount" when used to describe the amount of drug administered to a patient suffering from congestive heart failure, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that results in a therapeutically useful decrease in the symptoms of heart failure, i.e., the shortness of breath, edema, fatigue associated with the failing heart.

The term "effective amount" when used to describe therapy to a patient suffering from myelosuppression associated with cytotoxic chemotherapy, e.g., cancer chemotherapy or ionizing radiation therapy, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that increases blood cell production, particularly granulocyte production, thereby resulting in a therapeutically useful and selective reduction of the myelosuppression in the individual undergoing the chemotherapy or ionizing radiation therapy.

The term "effective amount" when used to describe therapy to a patient at elevated risk of developing myelosuppression due to a present or imminent administration of cytotoxic chemotherapy, e.g., cancer chemotherapy, or ionizing radiation therapy, in order to prevent the secondary myelosuppression associated therewith, refers to the amount of 1-(3-hydroxy-4-methoxyphenyl)-4-methyl-5-ethyl-7,8-dimethoxy-5H-2,3-benzodiazepine, or a pharmaceutically acceptable salt thereof that prevents, reduces or delays the reduction in blood cell production, particularly granulocyte production generally associated with such therapies.

The term "individual" or "subject" includes human beings and non-human animals. With respect to the disclosed methods of treating $LTB_4$ mediated inflammatory disorders, these terms refer, unless the context indicates otherwise, to an organism that is afflicted with such an inflammatory disorder.

The term "treatment" when used in association with a chronic or recurring disorder encompasses not only intervention in the disorder when it is presently active, but also refers to intervention to prevent or delay the onset of a chronic disorder or intervention to prevent or delay recurrence of the disorder.

With respect to disclosed methods of preventing or delaying the onset of a chronic disorder, these terms refer unless the context indicates otherwise, to an organism that is likely to be afflicted with a chronic disorder or that suffers from a disorder known to recur periodically. The selection of an individual likely to incur an inflammatory disorder may take into account the presence of inflammatory conditions that historically are known to have a high incidence of recurrence, such as, for example, IBD. The likelihood of incurring an inflammatory disorder may also be due to tissue insult that is known beforehand, such as a surgical procedure. The future inflammatory disorder may also result from a secondary effect of an initial tissue insult. An example of this is inflammation due to gout caused by elevated uric acid levels that occur secondary to lysis of a tumor mass following administration of cytotoxic chemotherapy or therapeutic radiation treatment.

The term "epilepsy" refers to any of various neurological disorders characterized by recurring attacks of motor, sensory, or psychic malfunction with or without loss of consciousness and with or without convulsive seizures.

The term "individual" or "subject" includes human beings and non-human animals. With respect to the disclosed methods of treating $LTB_4$ mediated inflammatory disorders, these terms refer, unless the context indicates otherwise, to an organism that is afflicted with such an inflammatory disorder.

With respect to disclosed methods of "preventing" or "delaying the onset" of $LTB_4$-mediated inflammatory disorders, these terms refer, unless the context indicates otherwise, to an organism that is likely to be afflicted with such an inflammatory disorder. The selection of an individual likely to incur such an inflammatory disorder may take into account the presence of inflammatory conditions that historically are known to have a high incidence of recurrence, such as, for example, IBD. The likelihood of incurring such an inflammatory disorder may also be due to tissue insult which is known beforehand, such as a surgical procedure. The future inflammatory disorder may also result from a secondary effect of an initial tissue insult. An example of this is inflammation due to gout caused by elevated uric acid levels that occur secondary to lysis of a tumor mass following administration of cytotoxic chemotherapy or therapeutic radiation treatment.

DETAILED DESCRIPTION OF THE INVENTION

According to the present invention, 1-(3,4-dimethoxyphenyl)-4-methyl-5-ethyl-7-methoxy-8-hydroxy-5H-2,3-benzodiazepine, and pharmaceutically acceptable salts thereof, interact with the $LTB_4$ receptor and are useful in methods of treatment or prevention of inflammatory disorders mediated by $LTB_4$.

Such inflammatory disorders include, but are not limited to, Inflammatory Bowel Disease, including Crohn's Disease and ulcerative colitis; psoriasis; gout, rheumatoid arthritis and radiation-induced gastrointestinal inflammation.

In addition, 1-(3,4-dimethoxyphenyl)-4-methyl-5-ethyl-7-methoxy-8-hydroxy-5H-2,3-benzodiazepine, and pharmaceutically acceptable salts thereof, interact with the $TXA_2$ receptor and are thus useful in methods of treatment or prevention of disease processes mediated by $TXA_2$ including, but not limited to pain, asthma, immune system activation of coagulation, angiogenesis associated with tumor development, and chronic inflammatory disorders Chronic inflammatory disorders mediated by $TXA_2$ include, for example, chronic fatigue syndrome/fibromyalgia (CFS/FM), infertility (recurrent fetal loss and fetal wastage syndromes), osteonecrosis of the jaw, multiple sclerosis (MS), depression, autism, Crohn's Disease, Inflammatory Bowel Disease (IBD), late Lyme Disease, Sjogren's Syndrome (SS), transient ischemic attack, attention deficit disorder and Parkinson's Disease.

1-(3,4-dimethoxyphenyl)-4-methyl-5-ethyl-7-methoxy-8-hydroxy-5H-2,3-benzodiazepine, and pharmaceutically acceptable salts thereof, have also demonstrated affinity for adenosine receptors in in vitro binding assays. This affinity for the adenosine receptor is an indicator that the compound has utility in methods of treatment of disorders whose etiology or progression is associated with a mechanism that is adenosine mediated.

Research has shown adenosine to be a mediator in numerous disorders For example adenosine is associated with central nervous system (CNS) disorders associated with elevated excitability of neurons. Compositions of the invention are believed to have anticonvulsant activity that is therapeutically useful in methods of treatment of a variety of CNS disorders associated with elevated neuronal activity. Epilepsy is one such disorder.

Adenosine is also implicated in CNS disorders involving decreased cerebral blood flow. Adenosine has been shown to increase cerebral blood flow.

Adenosine has been linked to CNS disorders involving increased release of excitatory amino acids such as aspartate. Such disorders are associated with the neuronal cell death subsequent to cerebral ischemia. One cause of cerebral ischemia is stroke.

Compositions of the invention are believed to be therapeutically useful as neuroprotective agents in methods of preventing neuronal cell death following an ischemic event in the CNS.

Adenosine has been linked to psychiatric disorders such as schizophrenia and anxiety disorders, and to neurodegenerative disorders such as Huntington's disease and Parkinson's Disease. Thus compositions of the invention are believed to be therapeutically useful in methods of treatment of Huntington's disease, Parkinson's disease, anxiety and schizophrenia.

Adenosine has been linked to sleep induction and wakefulness, thus compositions of the invention are believed to have therapeutic utility in methods of treatment of patents who would benefit from sleep induction or from an agent that promotes wakefulness.

Other studies have shown adenosine mediation in pain, including, but not limited to acute pain, chronic pain, neuropathic pain, surgical pain, cancer pain, trigeminal neuralgia, migraine, primary and secondary hyperalgesia, inflammatory pain, nociceptive pain, tabes dorsalis, phantom limb pain, spinal cord injury pain, central pain, post-herpetic pain, HIV pain, back pain, neck pain, dental pain, premenstrual pain, visceral pain, pain due to burns, migraine or cluster headaches, and neuralgias. Thus compositions of the invention are believed to be therapeutically useful in methods of treatment of individuals suffering from pain.

Studies have shown that some The $A_2$ receptor-specific adenosine analogues act to inhibit production of cytokines such as IL6. Thus, compositions of the invention are believed to be useful in methods of treatment of individuals who will benefit from administration of an agent that inhibits IL-6.

Studies have shown adenosine mediation in disorders including congestive heart failure, coronary artery disease, hypertension, renal failure, glaucoma and asthma. Thus, compounds of the invention are believed to be therapeutically useful in methods of treatment of individuals suffering from congestive heart failure, coronary artery disease, hypertension, renal failure, glaucoma or asthma.

Adenosine mediation has also been associated with the process of wound healing. It is believed that the compositions of the present invention may thus enhance wound healing. In addition, administration of 1-(3,4-dimethoxyphenyl)-4-methyl-5-ethyl-7-methoxy-8-hydroxy-5H-2,3-benzodiazepine prior to a known future wound such as a planned surgical procedure will accelerate recovery from surgery. Thus, 1-(3,4-dimethoxyphenyl)-4-methyl-5-ethyl-7-methoxy-8-hydroxy-5H-2,3-benzodiazepine, and pharmaceutically acceptable salts thereof, via interaction with adenosine receptors are believed to be useful: in methods of treatment by enhancing wound healing, e.g., enhancing wound healing in preparation for a surgical procedure.

Adenosine has also been implicated in the process of hair growth, thus compounds of the invention are believed to be therapeutically useful in methods of promoting hair growth in individuals needing such treatment.

Adenosine mediation has also been shown in myelosuppression such as that which occurs following ionizing radiation therapy or cytotoxic chemotherapy. Compositions containing 1-(3,4-dimethoxyphenyl)-4-methyl-5-ethyl-7-methoxy-8-hydroxy-5H-2,3-benzodiazepine may be used to treat such myelosuppression or to prevent myelosuppression when administered prior to or co-administered with radiotherapy or chemotherapy.

Adenosine has also been shown to mediate gastrointestinal tract relaxation. Such activity suggests that compositions described herein may be therapeutically useful in methods of treatment of irritable bowel syndrome.

Thus, 1-(3,4-dimethoxyphenyl)-4-methyl-5-ethyl-7-methoxy-8-hydroxy-5H-2,3-benzodiazepine, and pharmaceutically acceptable salts thereof, interact with adenosine receptors and are useful: in methods of treatment or prevention of disorders including, but not limited to, central nervous system disorders, e.g., epilepsy, conditions associated with decreased cerebral blood flow, conditions associated with increased release of excitatory amino acids, migraine, Huntington's disease, and Parkinson's Disease; congestive heart failure; coronary artery disease; hypertension; renal failure; glaucoma; asthma; myelosuppression secondary to cytotoxic chemotherapy or ionizing radiation therapy; pain, including migraine; chronic inflammatory disorders, all of which are believed to be mediated by adenosine. Examples of disorders associated with decreased cerebral blood flow and/or increased release of excitatory amino acids include neuronal damage associated with cerebral ischemia and stroke.

In addition, 1-(3,4-dimethoxyphenyl)-4-methyl-5-ethyl-7-methoxy-8-hydroxy-5H-2,3-benzodiazepine, and pharmaceutically acceptable salts thereof, via interaction with adenosine receptors are believed useful: in methods of promoting hair growth, methods of modulating sleep induction or wakefulness, and methods of neuroprotection.

Preparation of 1-(3,4-dimethoxyphenyl)-4-methyl-5-ethyl-7-methoxy-8-hydroxy-5H-2,3-benzodiazepine The 1-(3,4-dimethoxyphenyl)-4-methyl-5-ethyl-7-methoxy-8-hydroxy-5H-2,3-benzodiazepine useful in the present invention may be prepared by one of several methods. These methods generally follow the synthetic strategies and procedures used in the synthesis of 2,3-benzodiazepines such as tofisopam and tofisopam analogs. See U.S. Pat. Nos. 3,736,315 and 4,423,044 (tofisopam syntheses) and Horvath et al., *Progress in Neurobiology* 60(2000) p. 309-342 and references cited therein (preparation of tofisopam and analogs thereof), the entire disclosures of which are incorporated herein by reference. See also Kórósi et al., U.S. Pat. No. 4,322,346, the entire disclosure of which is incorporated herein by reference, disclosing three variations of the reaction protocol for preparing a substituted 2,3-benzodiazepine from the precursor benzopyrilium salt. A similar synthetic sequence for preparation of 2,3-benzodiazepines is disclosed in U.S. Pat. No. 3,736,315, the entire disclosure of which is incorporated herein by reference. Alternative methods for preparation of intermediate H start with an aryl acetonide or indanone starting material. See Kunnetsov, E. V., and Dorofeenko, G. N., *Zh. Org. Khim.*, 6, 578-581. and M. Vajda, *Acta Chem. Acad. Sci. Hung.*, 40, p. 295-307, 1964, respectively.

In the synthesis methods referenced above, the product of the chemical synthesis is racemic 1-(3,4-dimethoxyphenyl)-4-methyl-5-ethyl-7-methoxy-8-hydroxy-5H-2,3-benzodiazepine. This racemic mixture may be subsequently separated using known methods of resolution to produce (R)-1-(3,4-dimethoxyphenyl)-4-methyl-5-ethyl-7-methoxy-8-hydroxy-5H-2,3-benzodiazepine substantially free of the corresponding (S)-enantiomer, and (S)-1-(3,4-dimethoxyphenyl)-4-methyl-5-ethyl-7-methoxy-8-hydroxy-5H-2,3-benzodiazepine substantially free of the corresponding (R)-enantiomer.

Resolution of 1-(3,4-dimethoxyphenyl)-4-methyl-5-ethyl-7-methoxy-8-hydroxy-5H-2,3-benzodiazepine.

The synthetic procedures shown (or referenced) above result in racemic 1-(3,4-dimethoxyphenyl)-4-methyl-5-ethyl-7-methoxy-8-hydroxy-5H-2,3-benzodiazepine. The racemate must be resolved in order to isolate the individual (R)- and (S)-enantiomers of 1-(3,4-dimethoxyphenyl)-4-methyl-5-ethyl-7-methoxy-8-hydroxy-5H-2,3-benzodiazepine. Enantiomeric resolution may be achieved by converting racemic 1-(3,4-dimethoxyphenyl)-4-methyl-5-ethyl-7-methoxy-8-hydroxy-5H-2,3-benzodiazepine to a pair of diastereomers by either covalently bonding to an optically active moiety, or by salt formation with an optically active base or acid. Either of these two methods provides a molecule with a second chiral center, thus generating a pair of diastereomers. This diastereomeric pair is then separated by conventional methods such as for example, crystallization or chromatography.

Racemic 1-(3,4-dimethoxyphenyl)-4-methyl-5-ethyl-7-methoxy-8-hydroxy-5H-2,3-benzodiazepine may be converted to the (S)-dibenzoyltartaric acid salt, which is a diastereomeric mixture of SS and RS configurations. The pair of diastereomers (R,S) and (S,S) possess different properties, e.g., differential solubilities, that allow for the use of conventional separation methods. Fractional crystallization of diastereomeric salts from a suitable solvent is one such separation method. This resolution has been successfully applied to the resolution of racemic tofisopam. See Hungarian Patent 178516 and also Toth et al., *J. Heterocyclic Chem.*, 20:09-713 (1983), the entire disclosures of which are incorporated herein by reference.

Alternatively, racemic-1-(3,4-dimethoxyphenyl)-4-methyl-5-ethyl-7-methoxy-8-hydroxy-5H-2,3-benzodiazepine may be derivatized via, for example, acylation of the 3'-hydroxy moiety with a chiral acylating reagent such as, for example, (S)-mandelic acid. The resulting ester, has a second chiral center, and thus exists as a diastereomeric pair separatable using conventional methods such as crystallization or chromatography. Following the separation, the chiral moiety with which 1-(3,4-dimethoxyphenyl)-4-methyl-5-ethyl-7-methoxy-8-hydroxy-5H-2,3-benzodiazepine was derivatized, may be removed.

Racemic 1-(3,4-dimethoxyphenyl)-4-methyl-5-ethyl-7-methoxy-8-hydroxy-5H-2,3-benzodiazepine may be separated without diastereomer formation by differential absorption on a chiral stationary phase of a chromatography column, particularly a preparative HPLC column. Chiral HPLC columns are commercially available with a variety of packing materials to suit a broad range of separation applications. Exemplary stationary phases suitable for resolving the racemic 2,3-benzodiazepines include:

(i) macrocyclic glycopeptides, such as silica-bonded vancomycin which contains 18 chiral centers surrounding three pockets or cavities;
(ii) chiral $\alpha_1$-acid glycoprotein;
(iii) human serum albumin; and
(iv) cellobiohydrolase (CBH).

Chiral $\alpha_1$-acid glycoprotein is a highly stable protein immobilized onto spherical silica particles that tolerates high concentrations of organic solvents, high and low pH, and high temperatures. Human serum albumin, though especially suited for the resolution of weak and strong acids, zwitterionic and nonprotolytic compounds, has been used to resolve basic compounds. CBH is a very stable enzyme which has been immobilized onto spherical silica particles and is preferentially used for the separation of enantiomers of basic drugs from many compound classes.

The resolution of tofisopam by chiral chromatography using macrocyclic glycopeptide as a stationary phase on a Chirobiotic V™ column (ASTEAC, Whippany, N.J.) is disclosed in U.S. Pat. No. 6,080,736. Fitos et al. (*J. Chromatogr.*, 709 265 (1995)), discloses another method for resolving racemic tofisopam by chiral chromatography using a chiral $\alpha_1$-acid glycoprotein as a stationary phase on a CHIRAL-AGP™ column (ChromTech, Cheshire, UK). The latter method separates the (R)- and (S)-enantiomers and also resolves the two conformers (discussed below) of each enantiomer. These chromatographic methods, may be used generally to separate racemic 2,3-benzodiazepines into individual (R)- and (S)-enantiomers. The Chirobiotic V™ column is available in a semi-preparative size as employed for the above separation 500 mm×10 mm). The stationary phase of the Chirobiotic V™ column is commercially available in bulk for packing of preparative chromatography columns with larger sample capacity.

(R)- and (S)-enantiomers of 2,3-benzodiazepines may also exist in two stable conformations that may be assumed by the benzodiazepine ring, as generally depicted below:

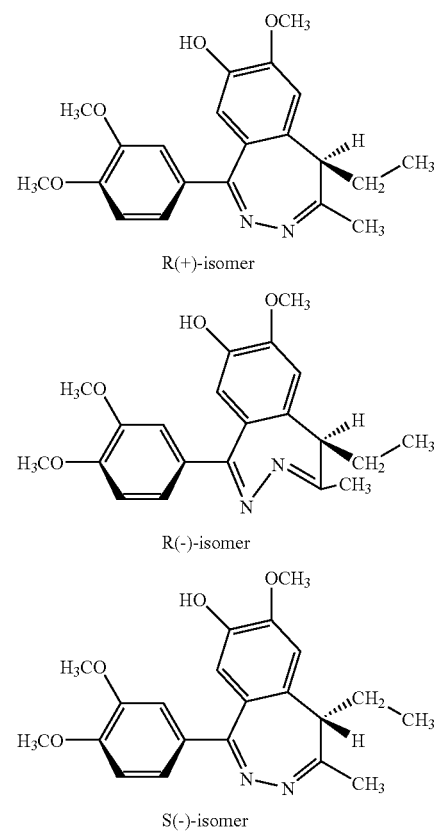

-continued

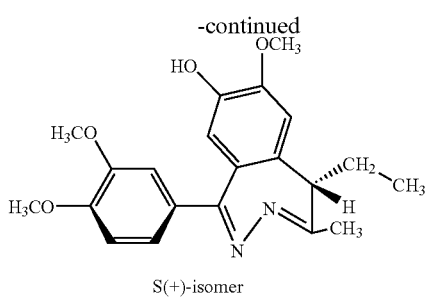

S(+)-isomer

The present invention includes compositions and methods as described herein that use any and all observable conformations of 1-(3,4-dimethoxyphenyl)-4-methyl-5-ethyl-7-methoxy-8-hydroxy-5H-2,3-benzodiazepine.

The compound used in the compositions and methods of the present invention may take the form of a pharmaceutically-acceptable salt. The term "salts", embraces salts commonly used to form alkali metal salts and to form addition salts of free acids or free bases. The term "pharmaceutically-acceptable salt" refers to salts that possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process or in the process of resolving enantiomers from a racemic mixture. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid.

Suitable pharmaceutically acceptable base addition salts of racemic-1-(3,4-dimethoxyphenyl)-4-methyl-5-ethyl-7-methoxy-8-hydroxy-5H-2,3-benzodiazepine, or the (R)- or (S)-enantiomer thereof, include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from 1-(3,4-dimethoxyphenyl)-4-methyl-5-ethyl-7-methoxy-8-hydroxy-5H-2,3-benzodiazepine by reacting, for example, the appropriate acid or base with 1-(3,4-dimethoxyphenyl)-4-methyl-5-ethyl-7-methoxy-8-hydroxy-5H-2,3-benzodiazepine.

The compounds useful in the compositions and methods of the invention may be administered to individuals (mammals, including animals and humans) afflicted with $LTB_4$-mediated inflammatory disorders or adenosine-mediated myelosuppression secondary to cytotoxic chemotherapy or ionizing radiation therapy, or disorders mediated by $TXA_2$. The latter include, but not limited to, pain, asthma and tumor development which involves angiogenesis mediated by $TXA_2$.

For treating or preventing inflammatory disorders mediated by $LTB_4$, or for treating disorders mediated by $TXA_2$, or for treating disorders mediated by adenosine, the specific dose of racemic-1-(3,4-dimethoxyphenyl)-4-methyl-5-ethyl-7-methoxy-8-hydroxy-5H-2,3-benzodiazepine, or an enantiomer thereof, to obtain therapeutic benefit, is determined by the particular circumstances of the individual patient including, the size, weight, age and sex of the patient. Also determinative is the nature and stage of the disease and the route of administration. Generally, a daily dosage of from about 100 to 1500 mg/day may be utilized. Preferably, a daily dosage of from about 100 to 1000 mg/day may be utilized. More preferably, a daily dosage of from about 100 to 500 mg/day may be utilized. Higher or lower doses are also contemplated.

For prophylactic administration, the compound should be administered far enough in advance of a known event that increases the chance of an inflammatory disorder mediated by $LTB_4$ such that the compound is able to reach the site of action in sufficient concentration to exert an effect modulating $LTB_4$ activity. The pharmacokinetics of specific compounds may be determined by means known in the art and tissue levels of a compound in a particular individual may be determined by conventional analyses.

Likewise, for prophylaxis involving a disorder mediated by $TXA_2$, the timing of compound administration should take into account factors relating to a recurrent condition such as asthma, and to events reasonably expected to trigger pain, symptoms, such as post-operative pain or pain caused by a progressive disorder.

The compositions of the present invention comprise a pharmaceutically acceptable carrier and: (i) racemic-1-(3,4-dimethoxyphenyl)-4-methyl-5-ethyl-7-methoxy-8-hydroxy-5H-2,3-benzodiazepine, (ii) (R)-1-(3,4-dimethoxy-phenyl)-4-methyl-5-ethyl-7-methoxy-8-hydroxy-5H-2,3-benzodiazepine substantially free of the corresponding (S)-enantiomer, (iii) (S)-1-(3,4-dimethoxyphenyl)-4-methyl-5-ethyl-7-methoxy-8-hydroxy-5H-2,3-benzodiazepine substantially free of the corresponding (R)-enantiomer, or a pharmaceutically acceptable salt of (i), (ii) or (iii). The active ingredient in such formulations may comprise from 0.1 to 99.99 weight percent. By "pharmaceutically acceptable carrier" is meant any carrier, diluent or excipient that is compatible with the other ingredients of the formulation and not deleterious to the recipient.

The compound may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time. For antiinflammatory use, the drug may be localized in a depot for controlled release to the circulation, or controlled release to a local site of inflammation.

The pharmaceutically acceptable carrier is selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions of the present invention may also be formulated so as to provide slow or controlled-release of the active ingredient therein. In general, a controlled-release preparation is a composition capable of releasing the active ingredient at the required rate to maintain constant pharmacological activity for a desirable period of time. Such dosage forms may provide a supply of a drug to the body during a predetermined period of time and thus maintain drug levels in the therapeutic range for longer periods of time than other non-controlled formulations.

For example, U.S. Pat. No. 5,674,533 discloses controlled-release compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 discloses a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 discloses controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. The patents cited above are incorporated herein by reference.

Biodegradable microparticles may be used in the controlled-release formulations of this invention. For example, U.S. Pat. No. 5,354,566 discloses a controlled-release powder that contains the active ingredient. U.S. Pat. No. 5,733,566 describes the use of polymeric microparticles that release antiparasitic compositions. These patents are incorporated herein by reference.

The controlled-release of the active ingredient may be stimulated by various inducers, for example pH, temperature, enzymes, water, or other physiological conditions or compounds. Various mechanisms of drug release exist. For example, in one embodiment, the controlled-release component can swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient (e.g., 1-(3,4-dimethoxyphenyl)-4-methyl-5-ethyl-7-methoxy-8-hydroxy-5H-2,3-benzodiazepine or a pharmaceutically-acceptable salt thereof) in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The practice of the invention is illustrated by the following non-limiting examples.

EXAMPLES

Example 1

Synthesis of racemic 1-(3,4-dimethoxyphenyl)-4-methyl-5-ethyl-7-methoxy-8-hydroxy-5H-2,3-benzodiazepine Racemic-1-(3,4-dimethoxyphenyl)-4-methyl-5-ethyl-7-methoxy-8-hydroxy-5H-2,3-benzodiazepine was synthesized according to the route of Scheme 1.

Scheme 1

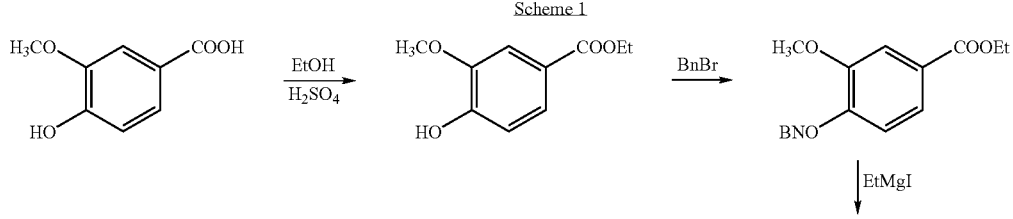

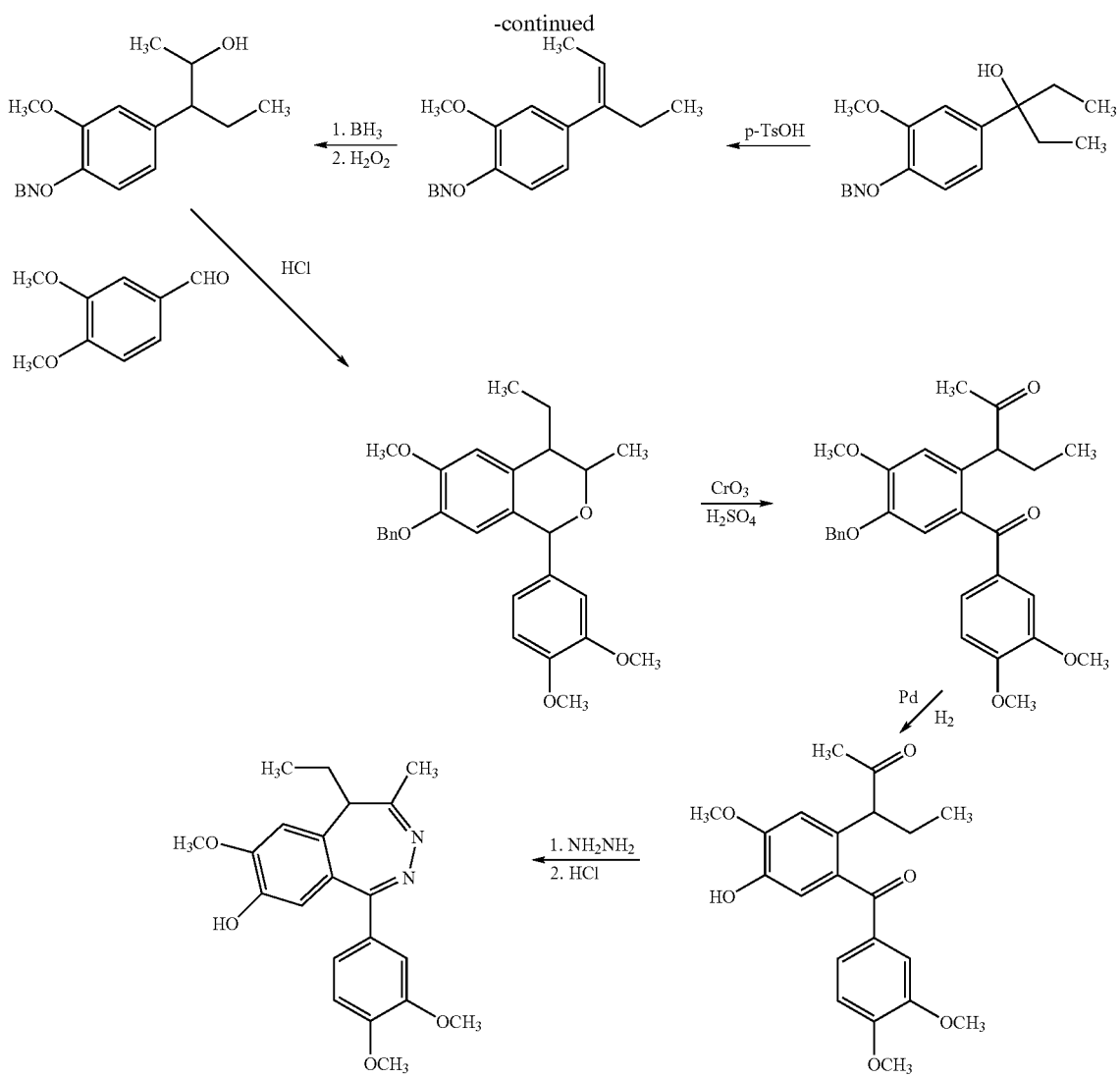

A. Esterification of 3-methoxy-4-hydroxybenzoic acid to yield ethyl-3-methoxy-4-hydroxybenzoate.

A solution of 100 g of 3-methoxy-4-hydroxybenzoic acid and 17 g of concentrated sulfuric acid in 300 mL of absolute ethanol was heated at reflux overnight. The mixture was concentrated and the residue poured into water. Methylene chloride was added and the solution washed successively with water, dilute sodium bicarbonate and water, then dried and concentrated. Yield: 118 g B. Benzylation of ethyl-3-methoxy-4-hydroxybenzoate to yield ethyl-3-methoxy-4-benzyloxybenzoate.

A solution of 118 g of ethyl-3-methoxy-4-hydroxybenzoate and 86 mL of benzyl bromide in 600 mL of acetone containing a suspension of 124 g of potassium carbonate was heated at reflux overnight. The mixture was filtered, the filtrate concentrated and the residue recrystallized from acetone.

C. Addition of ethyl magnesium iodide to ethyl-3-methoxy-4-benzyloxybenzoate to yield 3-(3-methoxy-4-benzyloxyphenyl)pentan-3-ol.

Iodoethane (112 mL) was added dropwise to a suspension of 35 g of magnesium turnings in 160 mL of ether. After the formation of ethyl magnesium iodide was complete, a solution of 142 g of ethyl 3-methoxy-4-benzyloxybenzoate in ether was added and the mixture was allowed to stir at room temperature for 3 days. The reaction was quenched by addition of saturated ammonium chloride. The layers were separated and the ether layer was dried and concentrated to an oily residue. Yield: 110 g.

D. Elimination of $H_2O$ from 3-(3-methoxy-4-benzyloxyphenyl)pentan-3-ol to yield 4-((1Z)-1-ethylprop-1-enyl)-1-benzyloxy-2-methoxybenzene.

A solution of 110 g of crude 3-(3-methoxy-4-benzyloxyphenyl)pentan-3-ol and 7 g of p-tolenesulfonic acid in 2L of benzene was heated at reflux for 4 hr with azeotropic removal of water. The mixture was then filtered through a pad of sodium bicarbonate and the filtrate concentrated. The residue was purified by column chromatography on neutral alumina.

E. Addition of $H_2O$ to 4-((1Z)-1-ethylprop-1-enyl)-1-benzyloxy-2-methoxybenzene to yield 3-(3-methoxy-4-benzyloxyphenyl)pentan-2-ol.

To a solution of 96 g of 4-((1Z)-1-ethylprop-1-enyl)-1-benzyloxy-2-methoxybenzene in tetrahydrofuran at 0° C.

was added 510 mL of a 1.0M solution of borane-tetrahydrofuran complex in tetrahydrofuran. The mixture was stirred for 3 hr at 0° C., then 204 mL of 25% hydrogen peroxide was added. The mixture was adjusted to pH 8 by addition of 5M sodium hydroxide and extracted with ether. The combined ether extracts were dried and concentrated. Yield: 102 g.

F. Reaction of 3-(3-methoxy-4-benzyloxyphenyl)pentan-2-ol with 3,4-dimethoxybenzaldehyde to yield 4-(4-ethyl-6-methoxy-7-benzyloxy-3-methyliso-chromanyl)-1,2-dimethoxybenzene.

A solution of 46 g of 3,4-dimethoxybenzaldehyde and 100 g of crude 3-(3-methoxy-4-benzyloxyphenyl)pentan-2-ol in 0.3L of dioxane was saturated with hydrogen chloride gas. The mixture was heated at reflux for 3 hr, then poured into water, basified with dilute sodium hydroxide and extracted with methylene chloride. The combined methylene chloride extracts were dried and concentrated.

G. Ring-opening of 4-(4-ethyl-6-methoxy-7-benzyloxy-3-methyliso-chromanyl)-1,2-dimethoxybenzene to yield 3-(4-benzyloxy-5-methoxy-2-{[3,4-dimethoxyphenyl]carbonyl}phenyl)pentan-2-one.

To a solution of 50 g of crude 4-(4-ethyl-6-methoxy-7-benzyloxy-3-methyliso-chromanyl)-1,2-dimethoxybenzene in acetone at 5° C. was added a solution of 50 g of chromic oxide in 500 mL of 35% sulfuric acid. The mixture was stirred at room temperature for 2 hr, neutralized by adding cold 10% sodium hydroxide and concentrated to remove acetone. Water was added and the mixture extracted with methylene chloride. The combined methylene chloride extracts were dried and concentrated. The residue was purified by column chromatography on silica gel. Yield: 18 g H. Debenzylation of 3-(4-benzyloxy-5-methoxy-2-{[3,4-dimethoxy-phenyl]carbonyl}phenyl)pentan-2-one to yield 3-{2-[(3,4-dimethoxy-phenyl)carbonyl]-4-hydroxy-5-methoxyphenyl}pentan-2-one.

A solution of 18 g of 3-(4-benzyloxy-5-methoxy-2-{[3,4-dimethoxy-phenyl]carbonyl}phenyl)pentan-2-one in methylene chloride containing a suspension of 2 g of 10% palladium on carbon was hydrogenated at 80 psi for 1 hr. The mixture was filtered through diatomaceous earth and the filtrate concentrated. Yield: 15 g I. Annulation of 3-{2-[(3,4-dimethoxy-phenyl)carbonyl]-4-hydroxy-5-methoxyphenyl}pentan-2-one by reaction with hydrazine to yield 1-(3,4-dimethoxyphenyl)-4-methyl-5-ethyl-7-methoxy-8-hydroxy-5H-2,3-benzodiazepine.

A solution of 14 g of 3-{2-[(3,4-dimethoxy-phenyl)carbonyl]-4-hydroxy-5-methoxyphenyl}pentan-2-one and 4.7 mL of hydrazine in 280 mL of ethanol was heated at reflux for 0.5 hr. After allowing the solution to cool to room temperature, it was saturated with HCl gas. The mixture was then concentrated to a volume of about 5 mL, basified with concentrated ammonium hydroxide, and extracted with methylene chloride. The combined methylene chloride extracts were dried and concentrated, and the residue recrystallized from ethyl acetate/hexane. Yield: 1.5 g The product 1-(3,4-dimethoxyphenyl)-4-methyl-5-ethyl-7-methoxy-8-hydroxy-5H-2,3-benzodiazepine was analyzed by HPLC, elemental analysis, GC/MS, proton NMR and differential scanning calorimetry (DSC). The data are as follows:

Purity: 98.36% by HPLC (% area). Column: Betasil Phenyl 4.6×150 mm. Mobile Phase: Acetonitrile::0.01M Phosphate Buffer (70::30). Flow Rate: 0.5 mL/min. Wavelength: 254 nm.

GC-MS; M/e=358; with the fragmentation pattern matching the proposed structure.

Differential scanning calorimetry (DSC): Temperature program 100° C. to 300° C. at 5° C./min, indicated molar purity=99.14% and melting point of 146.2° C.

Elemental analysis (calculated/analysis): % C −68.14/68.12; % H −6.63/6.63; N −7.43/7.20. The calculated values include 0.1M of residual ethyl acetate.

NMR (DCCl$_3$) (performed on GE QE 300): 1.08 ppm (t, 3H); 1.96 (s, 3H); 2.10 (m, 2H); 2.77 (m, 1H); 3.91 (s, 3H); 3.93 (s, 3H); 3.98 (s, 3H); 5.73 (bs, 1H); 6.70 (s, 1H); 6.80 (d, 1H); 6.95 (s, 1H); 7.00 (d, 1H); 7.58 (s, 1H).

Example 2

Resolution of 1-(3,4-dimethoxyphenyl)-4-methyl-5-ethyl-7-methoxy-8-hydroxy-5H-2,3-benzodiazepine The enantiomers of racemic-1-(3,4-dimethoxyphenyl)-4-methyl-5-ethyl-7-methoxy-8-hydroxy-5H-2,3-benzodiazepine are resolved by chiral chromatography as follows.

Racemic-1-(3,4-dimethoxyphenyl)-4-methyl-5-ethyl-7-methoxy-8-hydroxy-5H-2,3-benzodiazepine is loaded onto a semipreparative (500 mm×10 mm) Chirobiotic V column (ASTEC, Whippany, N.J.). Elution of the enantiomeric mixture with methyl-tert-butyl ether/acetonitrile (90/10 V/V), at a flow rate of 40 mL/min, is monitored at 310 nm. Fraction size is 10-20 mL and fractions are subjected to analytical chromatography using the same solvent composition on an analytical (150×4.6 mm) Chirobiotic V column. The fractions containing each isolated enantiomer are processed by removing the elution solvent in vacuo.

Example 3

Inhibition of LTB$_4$ Binding

The ability of 1-(3,4-dimethoxyphenyl)-4-methyl-5-ethyl-7-methoxy-8-hydroxy-5H-2,3-benzodiazepine to inhibit [$^3$H]LTB$_4$ binding to the LTB$_4$ receptor was determined as follows using the guinea pig spleen membrane assay of Cheng et al., *J. Pharmacol. Exp. Ther.*, 236(1), 126-132, 1986, the entire disclosure of which is incorporated herein by reference.

Reactions were carried out in a phosphate buffer (pH 7.4) containing NaCl, MgCl$_2$, EDTA, and bacitracin. The reaction volume of 150 µL containing 1.0 mg/mL of the Guinea pig spleen membrane preparation and 1 nM [$^3$H]LTB$_4$, with or without a candidate inhibitor, was incubated at 0-4° C. for 2 hours. Candidate inhibitors included the compounds listed in Table 1 and unlabeled LTB$_4$ as a control. The reaction was terminated by rapid vacuum filtration onto glass fiber filters. The filter was washed with cold buffer, dried and placed in a scintillation vial. Radioactivity trapped onto the filters was determined and compared to control values in order to ascertain any interactions of the test compound with the LTB$_4$ binding site.

As shown in Table 2, below, 1-(3,4-dimethoxyphenyl)-4-methyl-5-ethyl-7-methoxy-8-hydroxy-5H-2,3-benzodiazepine demonstrated a 36% inhibition of [$^3$H]LTB$_4$ binding to the LTB$_4$ receptor at a concentration of 10 µM.

These binding results indicate that 1-(3,4-dimethoxyphenyl)-4-methyl-5-ethyl-7-methoxy-8-hydroxy-5H-2,3-benzodiazepine is useful in the treatment and prevention of disorders which are mediated by LTB$_4$.

Example 4

TXA$_2$ Binding Assay

The ability of 1-(3,4-dimethoxyphenyl)-4-methyl-5-ethyl-7-methoxy-8-hydroxy-5H-2,3-benzodiazepine to inhibit the binding of [$^3$H]SQ 29,548 (30-60 Ci/mmol) was determined via the human platelet-based assay of Hedberg et al., "Characterization of [$^3$H]SQ 29,548 as a High Affinity Radioligand Binding to Thromboxane A$_2$—Receptors in Human Platelets.", *J. Pharmacol. Exp. Ther.* 245: 786-792 (1988), with modifications. TXA2 is a very unstable molecule, thus a surrogate ligand of known affinity for the TXA2 receptor is required as a standard for determination of binding affinity of new potential TXA$_2$ ligands. [$^3$H]SQ 29,548 is a ligand with known binding affinity for the TXA$_2$ receptor. [$^3$H]SQ 29,548 has been employed as a TXA2 ligand in several published studies, is accepted as a TXA2 binding standard, and is thus useful as a standard in assessing the binding affinity of new compounds to the TXA$_2$ receptor. See also, Armstrong, R. A., Jones, R. L., et al. "Ligand Binding to Thromboxane Receptors on Human Platelets: Correlation with Biological Activity." *Brit. Jrnl. Pharmac.* 79:953-964 (1983), the entire disclosures of which are incorporated herein by reference.

Reactions were carried out in 25 mM TRIS-HCl (pH 7.4) containing 138 mM NaCl, 5 mM KCl, 5 mM MgCl$_2$, 5.5 mM dextrose, and 2 mM EDTA at 25° C. for 60 minutes. Pinanethromboxane (K$_i$=149.0 nM) was employed as a competitor. The reaction was terminated by rapid vacuum filtration onto glass fiber filters. Radioactivity trapped onto the filters was determined and compared to control values in order to ascertain any interactions of test compound with the thromboxane A$_2$ binding site.

As shown in Table 2, below, 1-(3,4-dimethoxyphenyl)-4-methyl-5-ethyl-7-methoxy-8-hydroxy-5H-2,3-benzodiazepine demonstrated a 48.26% inhibition of [$^3$H] SQ 29,548 binding to the TXA$_2$ receptor at a concentration of 10 µM.

These binding results indicate that 1-(3,4-dimethoxyphenyl)-4-methyl-5-ethyl-7-methoxy-8-hydroxy-5H-2,3-benzodiazepine is useful in the treatment and prevention of disorders which are mediated by TXA$_2$.

Example 5

Adenosine Binding Assay

The ability of 1-(3,4-dimethoxyphenyl)-4-methyl-5-ethyl-7-methoxy-8-hydroxy-5H-2,3-benzodiazepine to inhibit the binding of [$^3$H]5'-N-ethylcarboxamidoadenosine (NECA) (15-30 Ci/mmol) was determined via the bovine striatal membrane assay of Bruns et al., "Characterization of the A2 Adenosine Receptor Labeled by [$^3$H]-NECA in Rat Striatal Membrane", *Pharmacology*, 29: 331-346 (1986), with modifications. See also, Weir et al. "Inhibition of N6-[$^3$H]CHA Binding by Carbamazepine" *Epilepsia*, 31(5), 503-512 (1990) with modifications; and Holtzman et al., "Role of Adenosine Receptors in Caffeine Tolerance," *J. Pharmacol. & Exp. Ther.*, 256(1), 62-67 (1990).

Reactions were carried out in 50 mM TRIS-HCl (pH 7.7) at 25° C. for 60 minutes. The reaction was terminated by rapid vacuum filtration onto glass fiber filters. Radioactivity trapped onto the filters was determined and compared to control values in order to ascertain any interactions of test compound with the adenosine binding site.

As shown in Table 2, below, 1-(3,4-dimethoxyphenyl)-4-methyl-5-ethyl-7-methoxy-8-hydroxy-5H-2,3-benzodiazepine demonstrated a 61.50% inhibition of [$^3$H]-NECA binding to the adenosine receptor at a concentration of 10 µM.

These binding results indicate that 1-(3,4-dimethoxyphenyl)-4-methyl-5-ethyl-7-methoxy-8-hydroxy-5H-2,3-benzodiazepine is useful in the treatment and prevention of disorders which are mediated by adenosine.

TABLE 2

Summary of [$^3$H]LTB$_4$ and TXA$_2$ binding data for 1-(3,4-dimethoxyphenyl)-4-methyl-5-ethyl-7-methoxy-8-hydroxy-5H-2,3-benzodiazepine compared with other 2,3-benzodiazepines

| Compound Name | TXA2 % inhibition @ 10 µM | LTB$_4$ % inhibition @ 10 µM | Adenosine non-selective @ 10 µM |
|---|---|---|---|
| 1-(3-hydroxy-4-methoxyphenyl)-4-methyl-5-ethyl-7,8-dimethoxy-5H-2,3-benzodiazepine | 25.95 | 63.94 | 4.26 |
| 1-(3,4-dimethoxyphenyl)-4-methyl-5-ethyl-7-methoxy-8-hydroxy-5H-2,3-benzodiazepine | 48.26 | 35.96 | 61.50 |
| 1-(3-methoxy-4-hydroxyphenyl)-4-methyl-5-ethyl-7,8-dimethoxy-5H-2,3-benzodiazepine | 1.98 | 49.89 | inactive |
| 1-(3,4-dimethoxyphenyl)-4-methyl-5-ethyl-7-hydroxy-8-methoxy-5H-2,3-benzodiazepine | 42.69 | 20.35 | 6.73 |
| 1-(3-methoxy-4-hydroxyphenyl)-4-methyl-5-ethyl-7-hydroxy-8-methoxy-5H-2,3-benzodiazepine | 44.02 | inactive | 22.40 |
| 1-(3-hydroxy-4-methoxyphenyl)-4-methyl-5-ethyl-7-hydroxy-8-methoxy-5H-2,3-benzodiazepine | 45.72 | inactive | 27.52 |

Example 6

Mouse Maximal Electroshock Test

In this model of tonic-clonic seizure activity, seizures were produced by application of an AC current via corneal electrodes. The maximal electroshock model is commonly employed to assay anticonvulsant activity. See, Swinyard et al., *J. Pharmacol. Exp. Therap.*, 1952, 106, 319-330; the entire disclosure of which is incorporated herein by reference. Numerous drugs known to be useful in treatment of disorders characterized by convulsive seizures have demonstrated activity in this model.

Forty test animals (Male Swiss mice, 31-38 g) were divided into six groups, as shown in Table 3.

TABLE 3

| Group | # of animals in test group | Treatment |
|---|---|---|
| A | 8 | Vehicle (solution of 15% DMSO, 35% PEG and 50% deionized water i.p |
| B | 5 | Diazepam (Reference standard) 20 mg/kg, i.p. |
| C | 8 | 1-(3,4-dimethoxyphenyl)-4-methyl-5-ethyl-7-methoxy-8-hydroxy-5H-2,3-benzodiazepine 15 mg/kg, i.p. |

TABLE 3-continued

| Group | # of animals in test group | Treatment |
|---|---|---|
| D | 8 | 1-(3,4-dimethoxyphenyl)-4-methyl-5-ethyl-7-methoxy-8-hydroxy-5H-2,3-benzodiazepine 30 mg/kg, i.p. |
| E | 8 | 1-(3,4-dimethoxyphenyl)-4-methyl-5-ethyl-7-methoxy-8-hydroxy-5H-2,3-benzodiazepine 45 mg/kg, i.p. |
| F | 3 | 1-(3,4-dimethoxyphenyl)-4-methyl-5-ethyl-7-methoxy-8-hydroxy-5H-2,3-benzodiazepine 60 mg/kg, i.p. |

Each animal was dosed with one of:

(1) diazepam, 20 mg/kg dissolved in normal saline as a reference standard;

(2) 1-(3,4-dimethoxyphenyl)-4-methyl-5-ethyl-7-methoxy-8-hydroxy-5H-2,3-benzodiazepine at a dose of 15, 30, 45 or 60 mg/kg; dissolved in 15% DMSO, 35% PEG and 50% deionized water (vehicle); or (3) vehicle comprising 15% DMSO, 35% PEG and 50% deionized water.

The concentrations of each of the dosed substances were normalized such that the volume of each dose was 10 mL/kg.

Approximately thirty minutes following administration of the above dose, full tonic-clonic seizures were induced in the animals by applying an AC current (50 Hz, 50 mA, 0.2 seconds) using an ECT unit 7800 (Ugo Basile, Comerio, Italy) through corneal electrodes. The appearance and duration of the induced seizures, as characterized by a tonic extension of hindlimbs past 90° were recorded. The seizure data are reproduced in Table 4 showing the seizure data as a mean with a standard error of the mean.

TABLE 4

| Group | Substance Dosed | Duration of tonic seizure Mean ± SEM (sec) |
|---|---|---|
| A | Vehicle | 11.1 ± 2.3 |
| B | Diazepam | 1.8 ± 0.7** |
| C | 1-(3,4-dimethoxyphenyl)-4-methyl-5-ethyl-7-methoxy-8-hydroxy-5H-2,3-benzodiazepine 15 mg/kg | 9.0 ± 2.5 |
| D | 1-(3,4-dimethoxyphenyl)-4-methyl-5-ethyl-7-methoxy-8-hydroxy-5H-2,3-benzodiazepine 30 mg/kg | 5.5 ± 1.1* |
| E | 1-(3,4-dimethoxyphenyl)-4-methyl-5-ethyl-7-methoxy-8-hydroxy-5H-2,3-benzodiazepine 45 mg/kg | 6.5 ± 1.7* |
| F | 1-(3,4-dimethoxyphenyl)-4-methyl-5-ethyl-7-methoxy-8-hydroxy-5H-2,3-benzodiazepine 60 mg/kg | 5.7 ± 1.8 |

*$p < 0.05$;
**$p < 0.01$ significance vs. vehicle (Mann Whitney U-test)

The results show that the compound 1-(3,4-dimethoxyphenyl)-4-methyl-5-ethyl-7-methoxy-8-hydroxy-5H-2,3-benzodiazepine demonstrated statistically significant anticonvulsant activity at the 30 and 45 mg/kg doses. The 60 mg dose showed comparable anticonvulsant activity, but fell short of statistical significance. This is likely a consequence of the small number of tested animals, All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A pharmaceutical composition comprising a pharmaceutically acceptable carrier and 1-(3,4-dimethoxyphenyl)-4-methyl-5-ethyl-7-methoxy-8-hydroxy-5H-2,3-benzodiazepine, or a pharmaceutically acceptable salt thereof.

2. The pharmaceutical composition according to claim 1, comprising (R)-1-(3,4-dimethoxyphenyl)-4-methyl-5-ethyl-7-methoxy-8-hydroxy-5H-2,3-benzodiazepine substantially free of the corresponding (S)-enantiomer; or a pharmaceutically acceptable salt thereof.

3. The composition according to claim 2 wherein the amount of (R)-1-(3,4-dimethoxyphenyl)-4-methyl-5-ethyl-7-methoxy-8-hydroxy-5H-2,3-benzodiazepine, or pharmaceutically acceptable salt thereof, in the composition is 85% by weight or more of the total weight of 1-(3,4-dimethoxyphenyl)-4-methyl-5-ethyl-7-methoxy-8-hydroxy-5H-2,3-benzodiazepine.

4. The composition according to claim 3 wherein the amount of (R)-1-(3,4-dimethoxyphenyl)-4-methyl-5-ethyl-7-methoxy-8-hydroxy-5H-2,3-benzodiazepine, or pharmaceutically acceptable salt thereof, in the composition is 90% by weight or more of the total weight of 1-(3,4-dimethoxyphenyl)-4-methyl-5-ethyl -7-methoxy-8-hydroxy-5H-2,3-benzodiazepine.

5. The composition according to claim 4 wherein the amount of (R)-1-(3,4-dimethoxyphenyl)-4-methyl-5-ethyl-7-methoxy-8-hydroxy-5H-2,3-benzodiazepine, or pharmaceutically acceptable salt thereof, in the composition is 95% by weight or more of the total weight of 1-(3,4-dimethoxyphenyl)-4-methyl-5-ethyl -7-methoxy-8-hydroxy-5H-2,3-benzodiazepine.

6. The composition according to claim 5 wherein the amount of (R)-1-(3,4-dimethoxyphenyl)-4-methyl-5-ethyl-7-methoxy-8-hydroxy-5H-2,3-benzodiazepine, or pharmaceutically acceptable salt thereof, in the composition is 99% by weight or more of the total weight of 1-(3,4-dimethoxyphenyl)-4-methyl-5-ethyl-7-methoxy-8-hydroxy-5H-2,3-benzodiazepine.

7. The pharmaceutical composition according to claim 1, comprising (S)-1-(3,4-dimethoxyphenyl)-4-methyl-5-ethyl-7-methoxy-8-hydroxy-5H-2,3-benzodiazepine substantially free of the corresponding (R)-enantiomer; or a pharmaceutically acceptable salt thereof.

8. The composition according to claim 7 wherein the amount of (S)-1-(3,4-dimethoxyphenyl)-4-methyl-5-ethyl-7-methoxy-8-hydroxy-5H-2,3-benzodiazepine, or pharmaceutically acceptable salt thereof, in the composition is 85% by weight or more of the total weight of 1-(3,4-dimethoxyphenyl)-4-methyl-5-ethyl-7-methoxy-8-hydroxy-5H-2,3-benzodiazepine.

9. The composition according to claim 8 wherein the amount of (S)-1-(3,4-dimethoxyphenyl)-4-methyl-5-ethyl-7-methoxy-8-hydroxy-5H-2,3-benzodiazepine, or pharmaceutically acceptable salt thereof, in the composition is 90% by weight or more of the total weight of 1-(3,4-dimethoxyphenyl)-4-methyl-5-ethyl -7-methoxy-8-hydroxy-5H-2,3-benzodiazepine.

10. The composition according to claim 9 wherein the amount of (S)-1-(3,4-dimethoxyphenyl)-4-methyl-5-ethyl-7-methoxy-8-hydroxy-5H-2,3-benzodiazepine, or pharmaceutically acceptable salt thereof, in the composition is 95% by weight or more of the total weight of 1-(3,4-dimethoxyphenyl)-4-methyl-5-ethyl-7-methoxy-8-hydroxy-5H-2,3-benzodiazepine.

11. The composition according to claim 10 wherein the amount of (S)-1-(3,4-dimethoxyphenyl)-4-methyl-5-ethyl-7-methoxy-8-hydroxy-5H-2,3-benzodiazepine, or pharmaceutically acceptable salt thereof, in the composition is 99% by weight or more of the total weight of 1-(3,4-dimethoxyphenyl)-4-methyl-5-ethyl -7-methoxy-8-hydroxy-5H-2,3-benzodiazepine.

12. The pharmaceutical composition according to claim 1, comprising a racemic mixture of the (R)- and (S)-enantiomers of 1-(3,4-dimethoxyphenyl)-4-methyl-5-ethyl-7-methoxy-8-hydroxy-5H-2,3-benzodiazepine, or a pharmaceutically acceptable salt thereof.

13. A method of treating a disorder characterized by convulsive seizures in an individual in need of such treatment, comprising administering to said individual a therapeutically effective amount of the composition according to claim 1 sufficient to inhibit convulsive seizures in said individual.

14. A method of treating a disorder characterized by convulsive seizures in an individual in need of such treatment, comprising administering to said individual a therapeutically effective amount of the composition according to claim 2 sufficient to inhibit convulsive seizures in said individual.

15. A method of treating a disorder characterized by convulsive seizures in an individual in need of such treatment, comprising administering to said individual a therapeutically effective amount of the composition according to claim 7 sufficient to inhibit convulsive seizures in said individual.

16. A method of treating a disorder characterized by convulsive seizures in an individual in need of such treatment, comprising administering to said individual a therapeutically effective amount of the composition according to claim 12 sufficient to inhibit convulsive seizures in said individual.

* * * * *